(12) United States Patent
Chapman et al.

(10) Patent No.: US 6,190,609 B1
(45) Date of Patent: Feb. 20, 2001

(54) METHODS AND APPARATUS FOR INACTIVATING CONTAMINANTS IN BIOLOGICAL FLUID

(75) Inventors: John R. Chapman, Lake Villa, IL (US); Peter R. H. Stark, Stoneham, MA (US); Michael V. Swallow, Chicago, IL (US); Dale N. Larson, Newton, MA (US)

(73) Assignee: Baxter International Inc., Deerfield, IL (US)

( * ) Notice: Under 35 U.S.C. 154(b), the term of this patent shall be extended for 0 days.

(21) Appl. No.: 09/081,168

(22) Filed: May 18, 1998

Related U.S. Application Data

(63) Continuation-in-part of application No. 08/752,606, filed on Nov. 19, 1996, now Pat. No. 5,922,278.

(51) Int. Cl.[7] ........................................................ A61L 2/00
(52) U.S. Cl. ........................ 422/24; 250/432 R; 422/28; 422/44; 435/283.1; 604/4
(58) Field of Search ................................ 422/24, 28, 44; 435/283.1, 2; 604/4; 250/432 R

(56) References Cited

U.S. PATENT DOCUMENTS

| 4,546,757 | * 10/1985 | Jakahi . |
| 4,608,255 | 8/1986 | Kahn et al. . |
| 4,726,949 | 2/1988 | Miripol et al. . |

(List continued on next page.)

FOREIGN PATENT DOCUMENTS

| B-63391/90 | 3/1993 | (AU) . |
| 0196515 | 3/1986 | (EP) . |
| 0491751 B1 | 9/1990 | (EP) . |
| WO 92/11057 | 12/1991 | (WO) . |

OTHER PUBLICATIONS

Matthews, et al., "Photodynamic therapy of viral contaminants with potential for blood banking applications," *Transfusions* 28: 81–83 (1988).

Rawal et al., "Reduction of human immunodeficiency virus–infected cells from donor blood by leukocyte filtration," *Transfusion*, vol. 29, No. 5, 460–462 (1989).

Judy, "Photodynamic Action of Viruses and in Potential Application for Blood Banking," *Newsletter of the Midwest Bio–Laser Institute*, pp. 1–6 (1989).

Bruisten et al., "Efficiency of white cell filtration and a freeze–thaw procedure for removal of HIV–infected cells from blood, "*Transfusion* 30: 833–837 (1990).

Rawal et al., "Dual Reduction in the Immunologic and Infectious Complications of Transfusion by Filtration/Removal of Leukocytes From Donor Blood Soon After Collection," *Transfusion Medicine Reviews*, pp. 36–41 (1990).

Taylor et al., "Human T–cell lymphotropic virus in volunteer blood donor", *Transfusion*, vol. 30, No. 9 (1990).

Wagner et al., "Approaches to the Reduction of Viral Infectivity in Cellular Blood Components and Single Donor Plasma", *Transfusion Medicine Reviews*, vol. V, No. 1, 18–32 (Jan. 1991).

Sadoff et al., "Experimental 6 $\log_{10}$ white cell–reduction filters for red cells," *Transfusion*, 32: 129–133 (1992).

(List continued on next page.)

*Primary Examiner*—Krisanne Thornton
(74) *Attorney, Agent, or Firm*—Andrew G. Kolomayets; Denise M. Serewicz; Amy L. H. Rockwell

(57) ABSTRACT

Apparatus and methods for treating a biological fluid with light and for inactivating contaminants in biological fluid. The biological fluid is contacted with a light source providing a high intensity light to the biological fluid. The biological fluid may include a quantity of a photochemical agent that when activated by light is operable to cause inactivation of at least some of the contaminants.

29 Claims, 15 Drawing Sheets

U.S. PATENT DOCUMENTS

| | | |
|---|---|---|
| 4,866,282 | 9/1989 | Miripol et al. . |
| 4,921,473 | 5/1990 | Lee et al. . |
| 4,952,812 | 8/1990 | Miripol et al. . |
| 5,030,200 | 7/1991 | Judy et al. . |
| 5,087,636 | 2/1992 | Jamieson et al. . |
| 5,184,020 | 2/1993 | Hearst et al. . |
| 5,269,946 | 12/1993 | Goldhaber et al. . |
| 5,290,221 | 3/1994 | Wolf, Jr. et al. . |
| 5,300,019 | 4/1994 | Bischof et al. . |
| 5,405,343 * | 4/1995 | Mohr .................................... 604/416 |
| 5,427,695 | 6/1995 | Brown . |
| 5,459,030 | 10/1995 | Lin et al. . |
| 5,503,721 | 4/1996 | Hearst et al. . |
| 5,527,704 | 6/1996 | Wolf, Jr. et al. . |
| 5,536,238 | 7/1996 | Bischof . |
| 5,545,516 | 8/1996 | Wagner . |
| 5,557,098 | 9/1996 | D'Silva . |
| 5,571,666 | 11/1996 | Floyd et al. . |
| 5,593,823 | 1/1997 | Wollowitz et al. . |
| 5,606,169 | 2/1997 | Hiller et al. . |
| 5,627,426 | 5/1997 | Whitman et al. . |
| 5,637,451 | 6/1997 | Ben-Hur et al. . |
| 5,683,661 | 11/1997 | Hearst et al. . |
| 5,691,132 | 11/1997 | Wollowitz et al. . |
| 5,709,991 | 1/1998 | Lin et al. . |

OTHER PUBLICATIONS

Eisenfeld et al., "Prevention of transfusion–associated cytomegalovirus infection in neonatal patients by the removal of white cells from blood," *Transfusion* 32: 205–209 (1992).

Tuite et al., "Photochemcial interactions of methylene blue and analogues with DNA and other biological substrates," *J. Photochem., Photobiol. B. Biol.*, 21, pp. 103–124 (1993).

Ben–Hur et al., "Inhibition of Phthalocyanine–sensitized Photochemolysis of Human Erythrocytes By Quercetin", Photochemistry and Photobiology, vol. 57, No. 6, 984–988 1993).

Ben–Hur et al., "Virus inactivation in red cell concentrates by photosensitization with phthalocyanines: protection of red cells but not of vesicular stomatitis virus with a water–soluble analogue of vitamin E", *Transfusion* vol. 35, No. 5 (1995).

Rywkin et al., "New Phthalocyannines for photodynamic virus inactivation in red bloodcell concentrates", Photochemistry and Photobiology, vol. 60, No. 2, 165–170 (1994).

Rywkin, et al., "Selective protection against IgG binding to red cells treated with phthalocyanines and red light for virus inactivation," *Transfusions*, vol. 35, No. 5 (1995).

Margolis–Nunno, et al., "Elimination of potential mutagenicity in platelet concentrates that are virally inactivated with psoralens and ultraviolet A light," *Transfusions*, 35: 855–862 (1995).

Wagner, et al., "Factors Affecting Virus Photoinactivation by a Series of Phenonthiazine Dyes," Photochemistry and Photobiology, 67(3): 343–349 (1998).

Ben–Hur, et al., "Photodynamic decontamination of blood for transfusion," New York Blood Center, 310 E. 67th Street, New York, NY 10021.

* cited by examiner

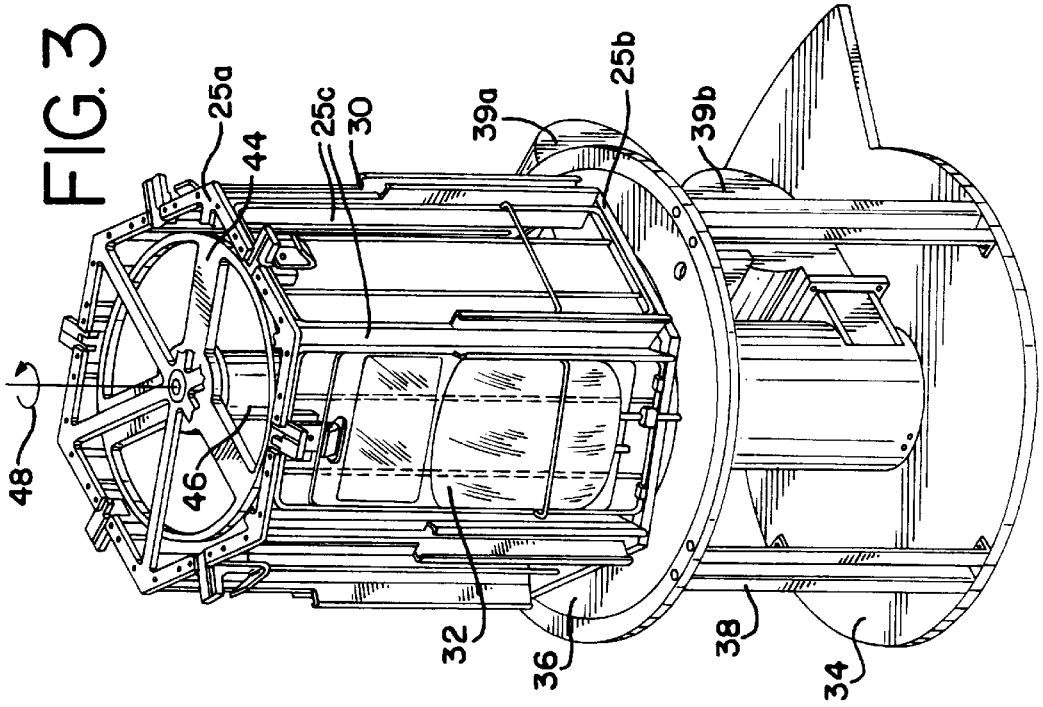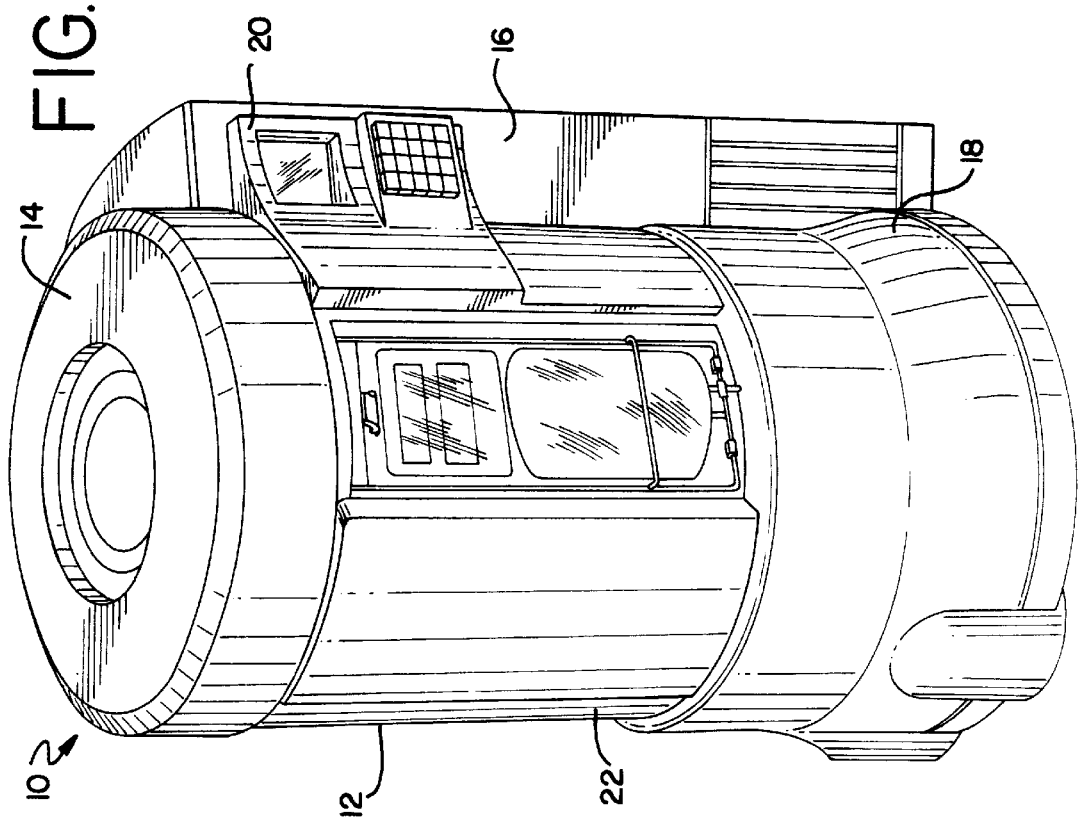

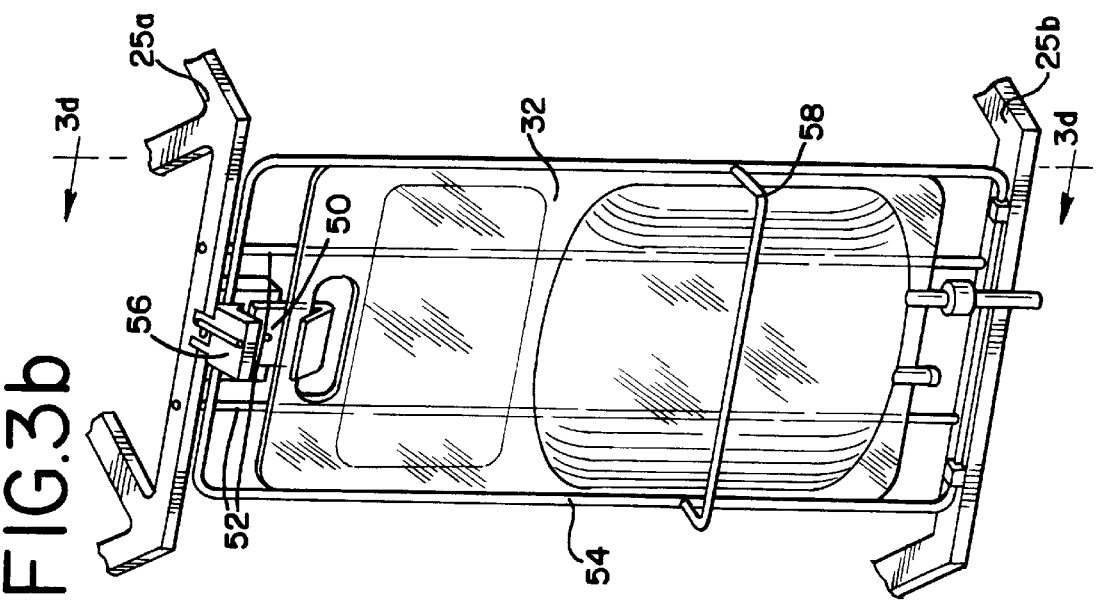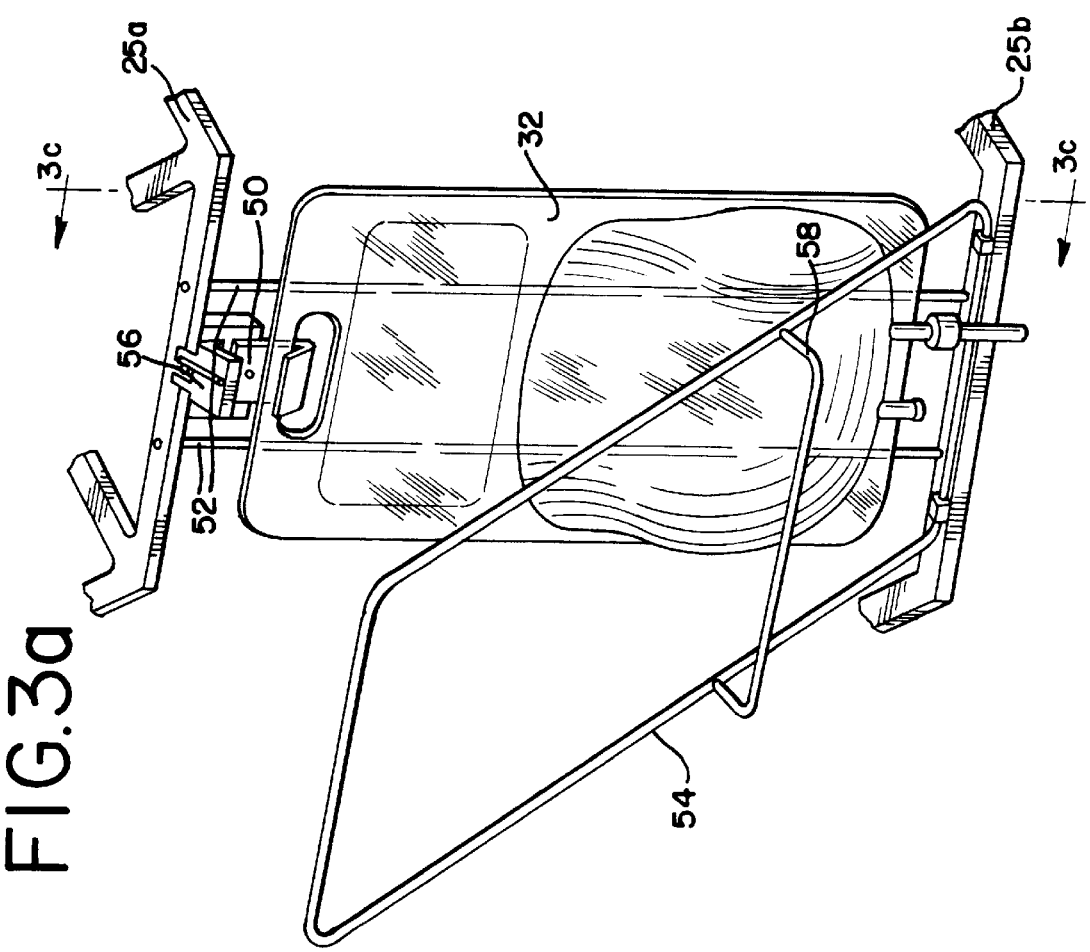

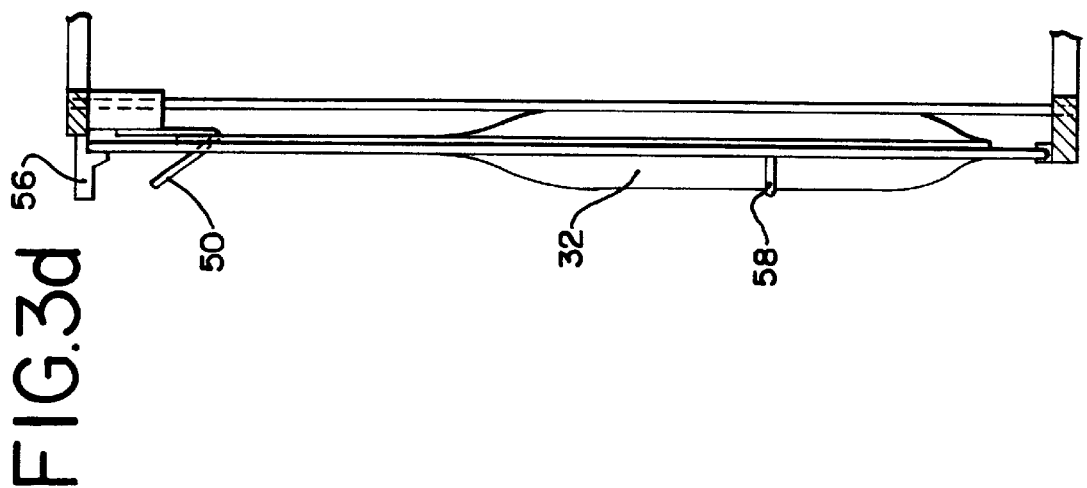
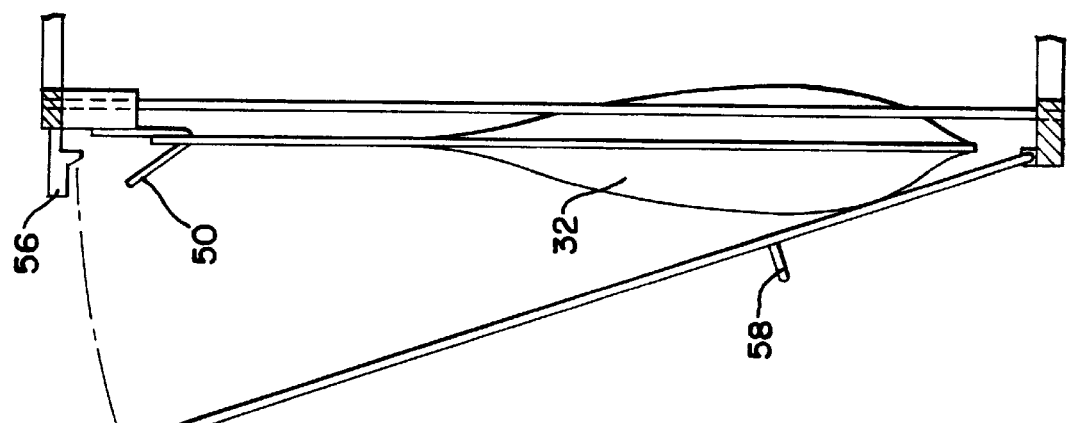

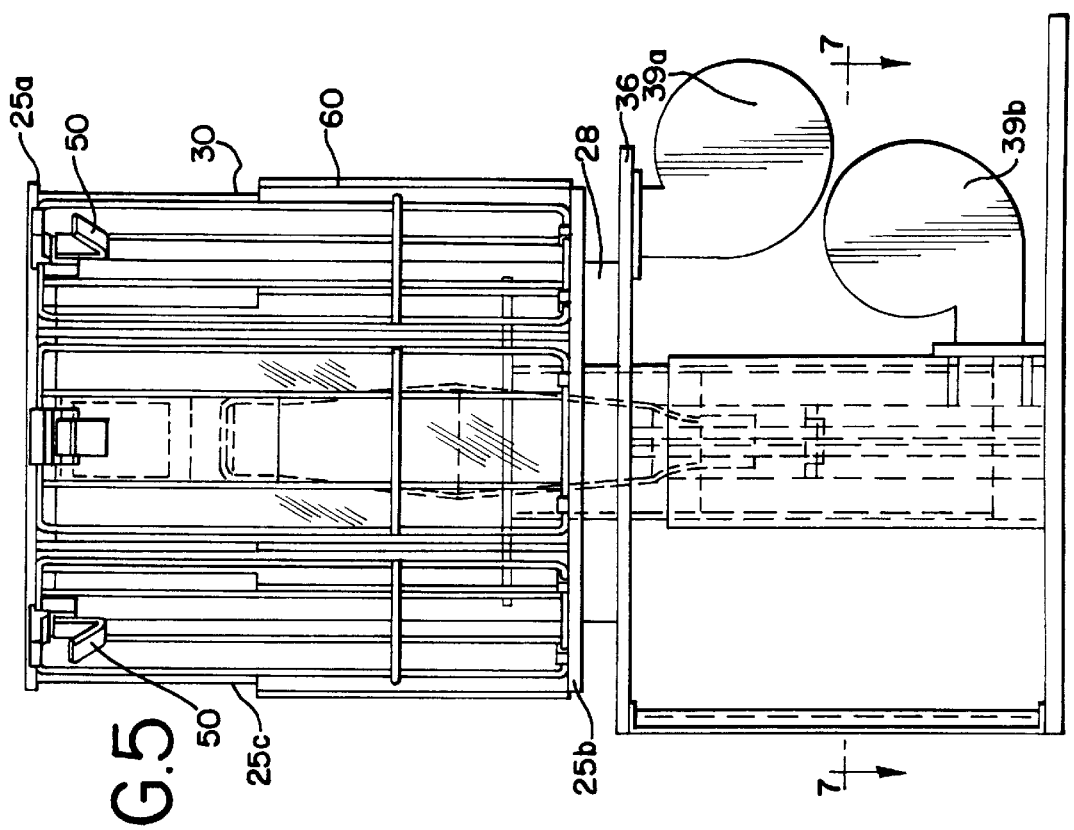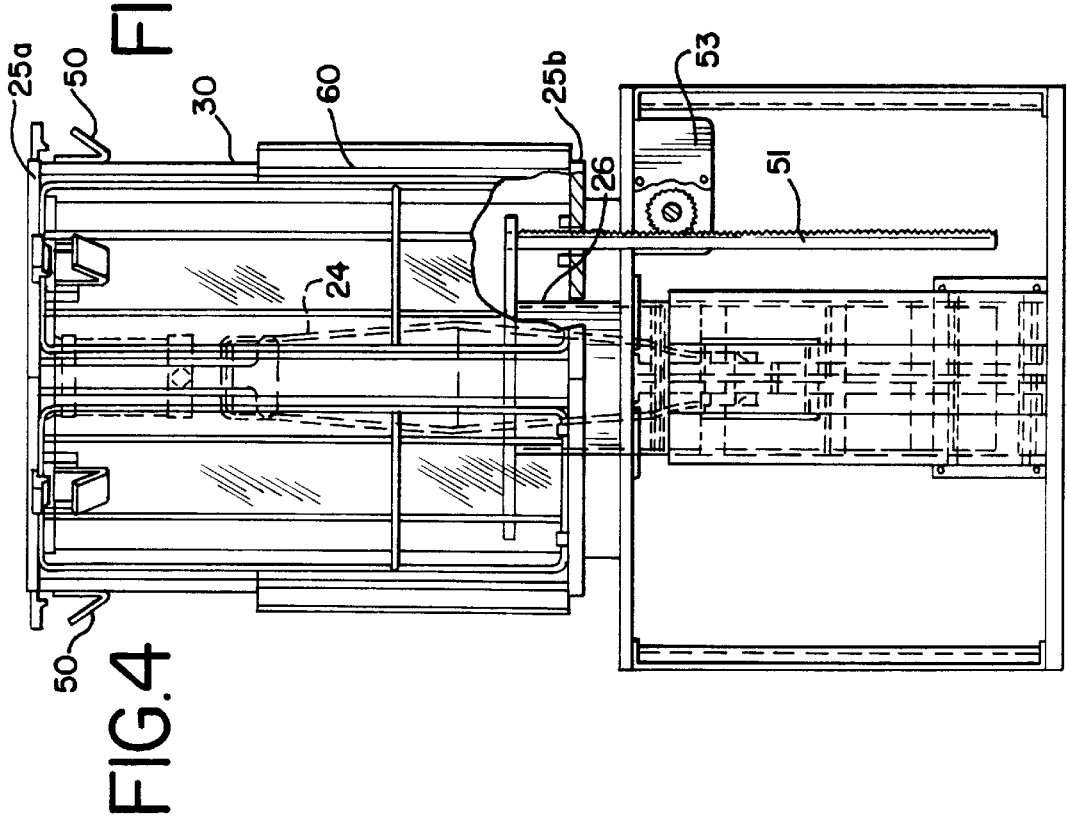

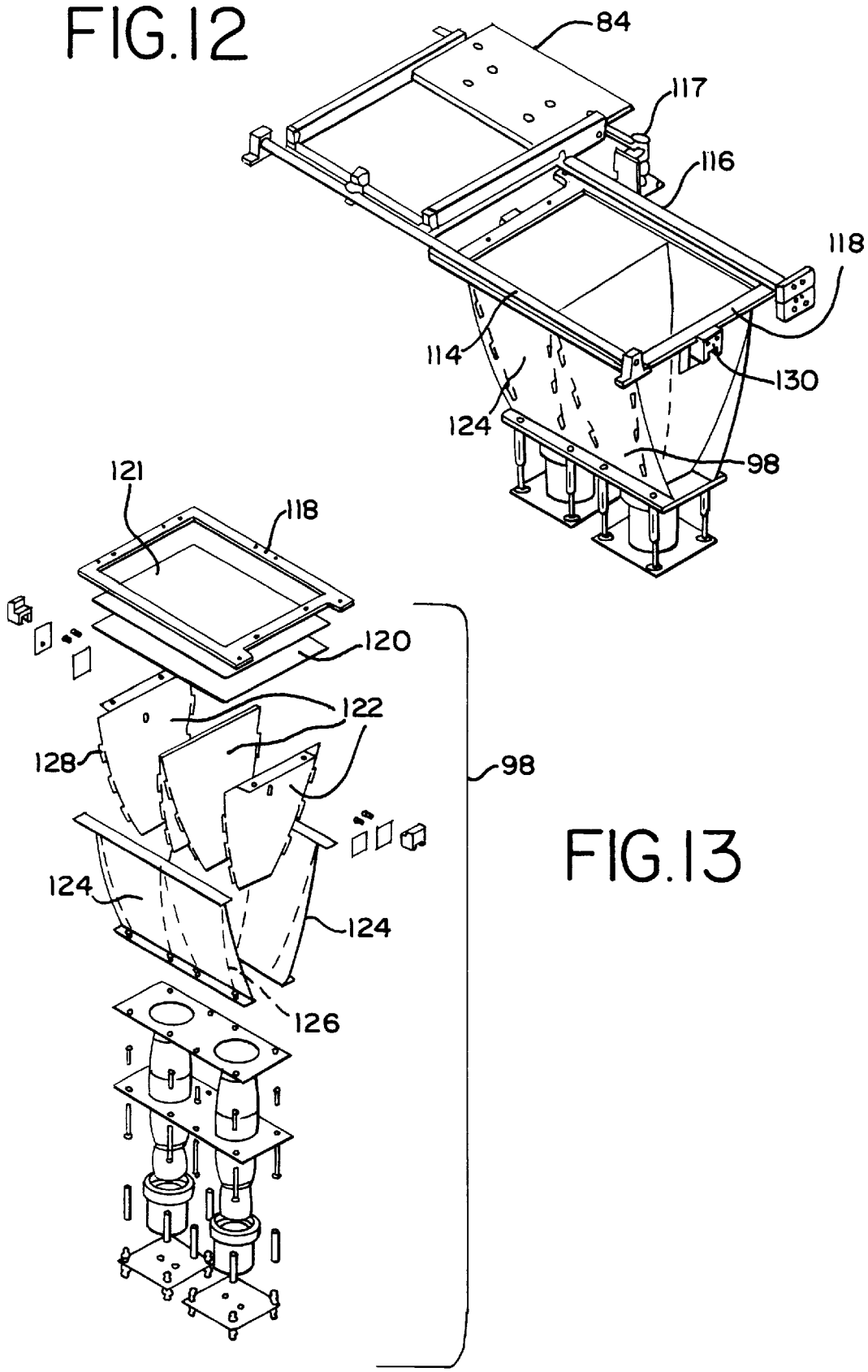

METHODS AND APPARATUS FOR INACTIVATING CONTAMINANTS IN BIOLOGICAL FLUID

This application is a continuation-in-part of U.S. application Ser. No. 08/752,606, filed on Nov. 19, 1996 now U.S. Pat. No. 5,922,278.

The present invention relates to methods and apparatus for treating biological fluids such as blood and blood components. More particularly, the present invention relates to methods and apparatus for inactivating contaminants, such as viruses, in such biological fluids.

Human blood includes both cellular and non-cellular components. The cellular components in blood include red blood cells (RBC), white blood cells (WBC), and platelets. Plasma is a non-cellular component of blood and is the liquid medium in which the cellular components are suspended. Plasma also includes various other components such as proteins (e.g. fibrinogen, albumin and globulins), electrolytes and metabolites.

It is well known that viruses, such as hepatitis or HIV virus, may be resident within human blood. The viruses residing in blood may be "intracellular," i.e. contained within one of the cellular components of blood, such as white blood cells, or they may be "extracellular" i.e. freely existing in the plasma. For example, the hepatitis virus is primarily an extracellular virus, the cytomegalovirus (the virus responsible for herpes) is primarily an intracellular virus, and the HIV virus (the virus responsible for AIDS) is found both intracellularly and extracellularly. Regardless of where the virus resides, the presence of the virus in the bloodstream poses the risk of infection and disease not only to the host, but also, if the blood or a blood component is collected and transfused, to a recipient.

Accordingly, the medical community has attempted to reduce the risk of transfusing blood that is tainted with active virus by developing methods and apparatus to remove virus from the blood stream or otherwise inactivate the virus. For example, one such attempt involves the filtration of blood and/or blood components to remove intracellular viruses entrained, for example, in white blood cells, Rawal et al., "Reduction of human immunodeficiency virus-infected cells from donor blood by leukocyte filtration," *Transfusion,* pp. 460–462 (1989). Although filtration of blood and/or blood components has been somewhat effective in removing the intracellular viruses, it has been generally ineffective in the removal of extracellular viruses because such viruses are typically too small to be captured by currently commercially available filters.

Other methods for inactivating viruses and, in particular, extracellular viruses, in blood, include steam sterilization of blood plasma to inactivate virus. Still, other methods include the use of "detergents" to cleanse the blood and/or the blood component of any viruses, or procedures whereby the blood components are frozen, thawed and washed to remove the virus.

A more recent approach to viral inactivation is the treatment of blood or blood components with a photochemical agent and light. When activated by light of an appropriate wavelength, the photochemical agent either kills the virus directly or indirectly inhibits the ability of the virus to replicate and, thus, in either case "inactivates" the virus. As used herein, the term "inactivate" (and forms thereof) mean the actual destruction, eradication of a contaminant such as a virus, or a direct or indirect effect on the contaminant that inhibits its ability to replicate or otherwise to adversely affect a living recipient.

Several known photochemical agents have been used or disclosed for use in inactivating viruses in blood. They include, for example, psoralens (which have been used in the inactivation of viruses in collected platelets) as described in U.S. Pat. No. 5,459,030. Other photochemical agents that have been disclosed for the inactivation of viruses in blood include the family of light activated drugs derived from benzoporphyrin, as described in U.S. Pat. No. 5,536,238, which is assigned to the assignee of the present application and is incorporated by reference herein. Still other photochemical agents considered for use in the inactivation of viruses in biological fluids are compounds from the family of phenothiazine dyes, which include, but are not limited to toluidine blue O, azure A, azure B, azure C, thionine, methylene blue, and methylene green.

For the photochemical agents to inactivate viruses, the light applied to the photochemical agent must be of a wavelength that can be absorbed by the photochemical agent. As described in U.S. Pat. No. 5,527,704, also assigned to the assignee of the present application and incorporated by reference herein, in the case of methylene blue, it is known that methylene blue absorbs visible light having wavelengths of between about 550 and 700 nm.

As presently understood, a methylene blue molecule that has been activated by light becomes a catalyst for secondary and tertiary reactions that inactivate virus. More specifically, activation of the photochemical agent such as methylene blue is believed to result in the production of singlet oxygen which enhances the secondary and tertiary reactions. A detailed discussion of methylene blue, its photophysics, and photodynamic action on proteins, nucleic acid, viruses and bacteria is set forth in Tuite et al., "Photochemical interactions of methylene blue and analogues with DNA and other biological substrates," *J. Photochem, Photobiol. B. Biol.,* 21, (1993) which is incorporated by reference herein.

In addition to acting as a catalyst for viral inactivation reactions, photochemical agents (when activated by light), such as methylene blue may also result in damage to plasma proteins and, in particular, therapeutic proteins as described in European Patent No. 0196515 which is incorporated by reference. As set forth in European Patent No. 0196515 and as used herein, therapeutic proteins include any biologically active protein which has qualities which make it useful in the treatment of medical disorders. Examples of such proteins include human-blood plasma proteins such as Factor VIII, Von Willebrand Factor, Factor IX, Factor X, Factor XI, Hageman Factor, the activated forms of such factors, prothrombin, anti-thrombin III, fibronectin, plasminogen, immune serum globulin, modified immune globulin, albumin, 1-antitrypsin, and prekallikrein. Prior to the present invention, a system capable of providing maximum viral kill with minimal damage to therapeutic proteins has been considered unattainable because the increased production of singlet oxygen was also believed to be responsible for protein damage.

Various apparatus for using photochemical agents in viral inactivation have also been developed. For example, in U.S. Pat. No. 5,300,019, assigned to the assignee of the present application and also incorporated by reference herein, an apparatus for treating a fluid containing a biological contaminant with a photochemical agent is described. In U.S. Pat. No. 5,300,019, blood including a contaminant, such as a virus, and a photochemical agent is pumped from a source container through a treatment chamber to a collection container. While in the treatment chamber, the blood is exposed to a light source that activates the photochemical agent as the blood is processed within the treatment chamber. To ensure that the blood is sufficiently and uniformly exposed to the light source, the blood (with contaminants and photochemical agent) is continuously mixed within the treatment chamber. After treatment, the blood is collected in the collection container. The photochemical agent described in that patent is benzoporphyrin.

In U.S. Pat. No. 5,527,704, also incorporated by reference, a single container of blood or a blood component is placed between two facing arrays of light emitting diodes. The container includes a blood component (plasma), a viral contaminant and a quantity of methylene blue. The container is irradiated by the light emitting diodes which produce light having a wavelength of approximately 620–670 nm to activate methylene blue. The container of blood or blood component is subjected to light for a period of approximately five (5) minutes.

While the prior art methods and apparatus represent progress in the inactivation of contaminants, such as viruses, in biological fluids, such as blood or blood components, there is still room for improvements. For example, one of the prime areas of concern is to better assure inactivation of a substantial portion of the contaminant with the goal being 100% inactivation. More specifically, it is desirable that exposure of the biological fluid to a light source provide maximum viral inactivation with minimal damage to the therapeutic proteins. Also, it is desirable that exposure of the biological fluid to a light source be of short duration to increase efficiency of treatment per light treatment and reduce the cost. It is further desirable that the exposure of the biological fluid to the light source be substantially uniform in its application and preferably without the need to continuously mix the blood and/or blood components. Because biological fluids such as blood or blood components are often collected or stored in plastic containers, it may also be further desirable to be able to treat more than one unit or container at a time to improve efficiency, but without adverse effect on the viral inactivation.

SUMMARY OF THE INVENTION

The present invention generally is embodied in method and apparatus for inactivating contaminants in a biological fluid. In accordance with one aspect of the present invention, the apparatus includes at least one wall defining a chamber and a quantity of biological fluid including one or more contaminants within the chamber. The biological fluid also includes a photochemical agent. The photochemical agent is operable to cause the inactivation of at least some of the contaminants upon exposure to a light source. To increase the inactivation effect of the photochemical agent, the apparatus includes a high intensity light source providing an intensity of at least 30 mW/cm². At least a portion of the wall of the chamber permits the light emitted by the light source to contact the fluid.

In accordance with another aspect of the present invention, the biological fluid is a component of blood, such as blood plasma, and the photochemical agent is a phenothiazine dye such as methylene blue. The light source may comprise a sodium light, and a control system may operably be connected to the light source and one or more sensors for providing that the light contacting the biological fluid is between about 1 and 100 Joules/cm².

In accordance with another aspect of the present invention, the chamber may be or may include a flexible plastic container, one or more of which are carried by a carriage relatively rotatable around the light source. To provide more complete and uniform light contact with the fluid, the light source may be elongated to provide light along the length of the source, in contrast, for example, to a point source light.

The present invention is also directed to an apparatus for treating a biological fluid with light wherein the apparatus includes a housing defining an interior chamber and a light source disposed within the chamber. The apparatus includes a fluid treatment region adapted to hold a predetermined quantity of biological fluid.

The present invention is also directed to an apparatus for inactivating contaminants in a biological fluid. The apparatus includes first and second light sources, each capable of providing light having an intensity of at least 30 mw/cm². A fluid treatment region is located between the first and second light sources.

In another aspect, the present invention is directed to a method for substantially inactivating contaminants in the biological fluid that is substantially free of red blood cells and includes a photochemical agent and other compounds. The method includes contacting the fluid with light having an intensity operative to activate the photochemical agent (and substantially at least about 30 mW/cm²) to inactivate the contaminants. In one aspect of the present invention, the biological fluid includes other compounds which, preferably, are not adversely affected by the light source. In another aspect of the present invention, the amount of light contacting the biological fluid and the time of contact are monitored and, if desired, controlled. This invention finds particular application when the biological fluid is blood plasma and the photochemical agent is methylene blue.

In another aspect, the present invention is directed to a method for substantially inactivating contaminants in a biological fluid by providing a quantity of a biological fluid and combining the biological fluid with a selected amount of a phenothiazine dye. The method further includes contacting the phenothiazine dye with light having an intensity of at least 30 mW/cm². The biological fluid may be contacted by the light for a period between approximately 0.3 and 30 minutes.

BRIEF DESCRIPTION OF THE DRAWINGS

FIG. 1 is a perspective view of the apparatus embodying the present invention;

FIG. 3 is a perspective view of the apparatus of FIG. 1, with the outer cover removed to show the interior of the apparatus;

FIG. 3a is a perspective view of a container suspended from a hook and the container holder in an open position;

FIG. 3b is a perspective view of the container of FIG. 3a with the container holder in a closed position;

FIG. 3c is a side view of a container suspended from a hook and the container holder in an open position;

FIG. 3d is a side view of the container of FIG. 3c with the container holder in a closed position;

FIG. 4 is an front elevational view of the apparatus of FIG. 3;

FIG. 5 is side elevational view of the apparatus of FIG. 3;

FIG. 12 is a perspective view of the tray and reflector subassemblies of the apparatus of FIG. 10;

FIG. 13 is an exploded, perspective view of the tray and reflector subassemblies of FIG. 12;

DETAILED DESCRIPTION OF THE DRAWINGS

Figure 2:
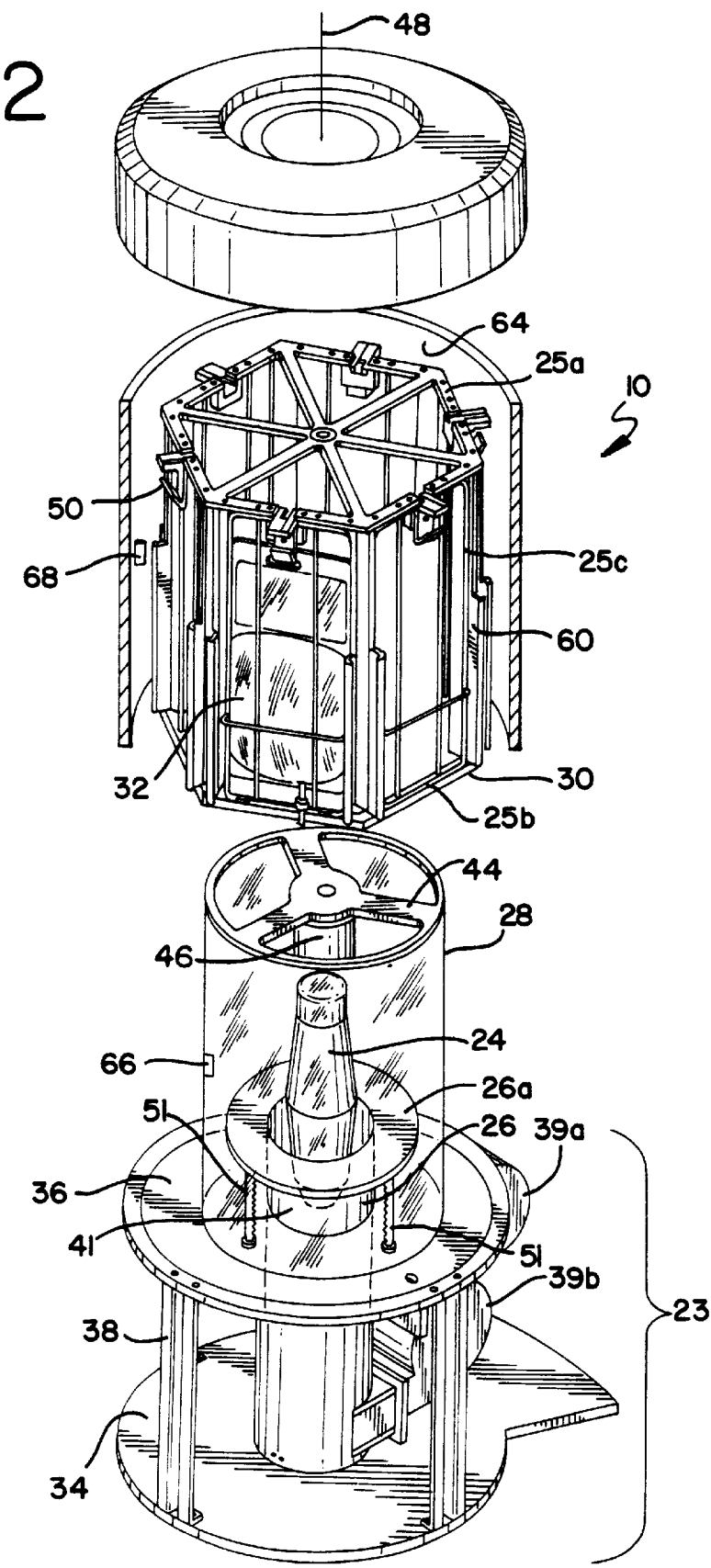
FIG. 2 is an exploded perspective view of the apparatus of FIG. 1, with portions of the outer cover removed for a better view of internal features.

Turning now to the drawings, one embodiment of the present invention is depicted in FIG. 1 as apparatus 10, sometimes referred to as a light box. As shown in FIG. 1, light box 10 includes a generally cylindrical housing 12 having a top portion or cover 14, a midportion 16, and a bottom portion 18. The midportion may include a control panel 20 for operator control of light box operation. A door 22 in the midportion allows access into the interior of the light box 10. Door 22 may be either hinged or, as shown in FIG. 1 slidable. Light box 10 may also include retractable spill tray (not shown) for collecting spilled liquid from within the light box 10.

FIG. 2 is an exploded view of the light box 10 and shows its basic component parts. Specifically, the illustrated light box 10 includes a base assembly 23, which supports a centrally located light source 24 and shutter assembly 26. A light transparent tube 28 rests on the base assembly and supports, at its upper end, a carriage assembly 30 for rotation about the transparent tube and light source. The carriage assembly is a generally cylindrical hexagonal framework for holding at least one substantially clear plastic container 32 containing biological fluid to be treated. To protect the user from undue exposure to the light source, the outer housing 12 and particularly the top and mid portions enclose the carriage and light source.

Turning first to the base assembly 23, the base assembly has a lowermost base plate 34 and a raised platform 36 supported above the base plate by rigid vertical support members 38. The space between the base plate and platform permits retraction of the shutter assembly 26, provides room for mounting cooling fans 39a and 39b for cooling different regions of the light box, and contains the mounting socket for the light source 24.

The light source 24 is generally centrally mounted on the base assembly 23 and more specifically on platform 36. The light source includes preferably an elongated tube to provide uniform illumination of the interior of the light box 10. Light source 24 may be any lamp or bulb, preferably capable of emitting a high intensity light.

More specifically, light source 24 may be any lamp or bulb that can provide light with a wavelength and intensity effective (a) to inactivate contaminants in the biological fluid to be treated, or more precisely (b) to activate the photochemical agent (if any) used in treating the biological fluid. For example, if the photochemical agent is methylene blue, the light source should be capable of providing more than 25% of its light in the visible spectrum in a wavelength range of approximately 550–700 nm to provide better efficiency and lower heat generation.

In addition, light source 24 should provide a high intensity light that is capable of providing maximum activation of the photochemical agent without significantly harming other desirable components in the biological fluid. For example, high intensity, as used herein means an intensity of at least 30 mW/cm$^2$ as measured at the biological fluid or container thereof. In the case of methylene blue, for example, the intensity should be at least 30 mW/cm$^2$ and, preferably between 85–130 mW/cm$^2$ measured at the biological fluid (or container thereof) and in a wavelength range from 550–700 nm. Of course, other photochemical agents may be operable at different intensities and wavelengths. Examples of light sources that can be used to activate photochemical agents include high pressure sodium lamps, halogen lamps, sulphur lamps, metal halide lamps or xenon lamps. One such lamp is the high pressure sodium vapor lamp that includes a ceramic arc tube, such as alumina ($Al_2O_3$), in a clear or coated outer bulb with a medium or mogul screwbase for mounting into socket (in base assembly 23). Such a sodium lamp is sold by Phillips Lighting under the tradename Ceramalux, Model No. C1000S52.

To protect the light source and the user, as shown in FIGS. 2, 3 and 4, light box 10 includes retractable shutter assembly 26 that encloses the light source 24 during, for example, loading and start-up procedures and retracts after loading is complete and the light is fully energized. The shutter assembly 26 comprises a cylindrical tube 41 that, when raised, shields the light source. The tube has an upper radial flange 26a which mounts to the shutter arms 51. Movement of the shutter is effected by shutter drive motor 53 as shown in FIG. 4, in a rack and pinion gear.

As noted above, the top of shutter 26 includes a top flange 26a that, when shutter 26 is retracted covers most of the portion of platform 36 within tube 28. The upper surface of 26a is reflective to further distribute light to the interior of the light box. The flange is preferably coated with a highly reflective material, such as White 91 sold by Alcoa Brite Products.

Figure 6:
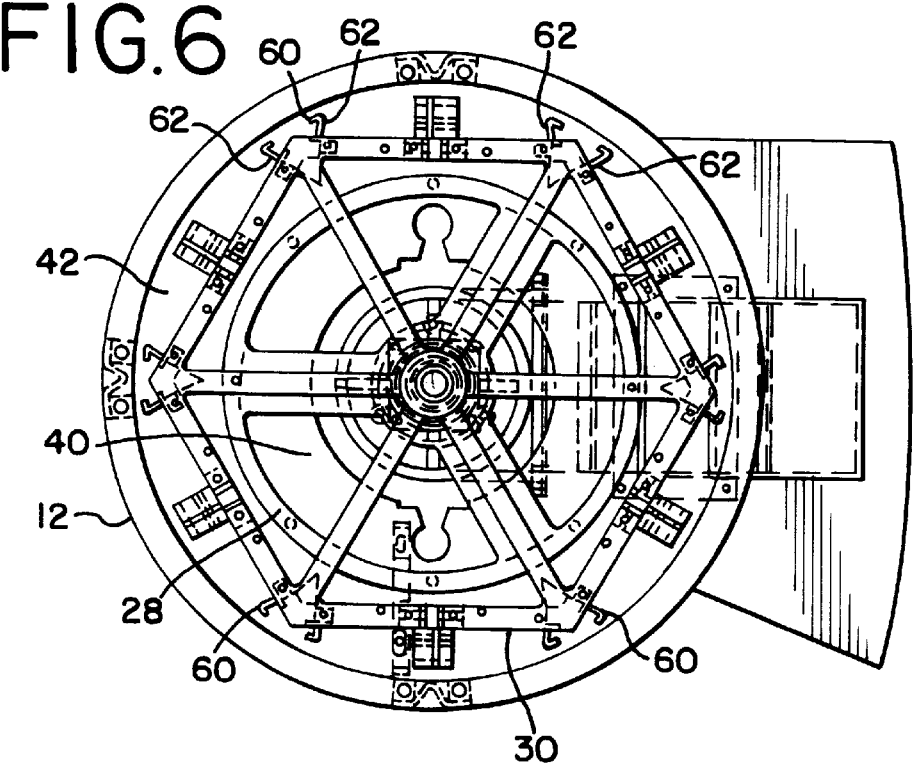
FIG. 6 is a top view of the apparatus of FIG. 1, with the top of the outer housing removed.
Figure 7:
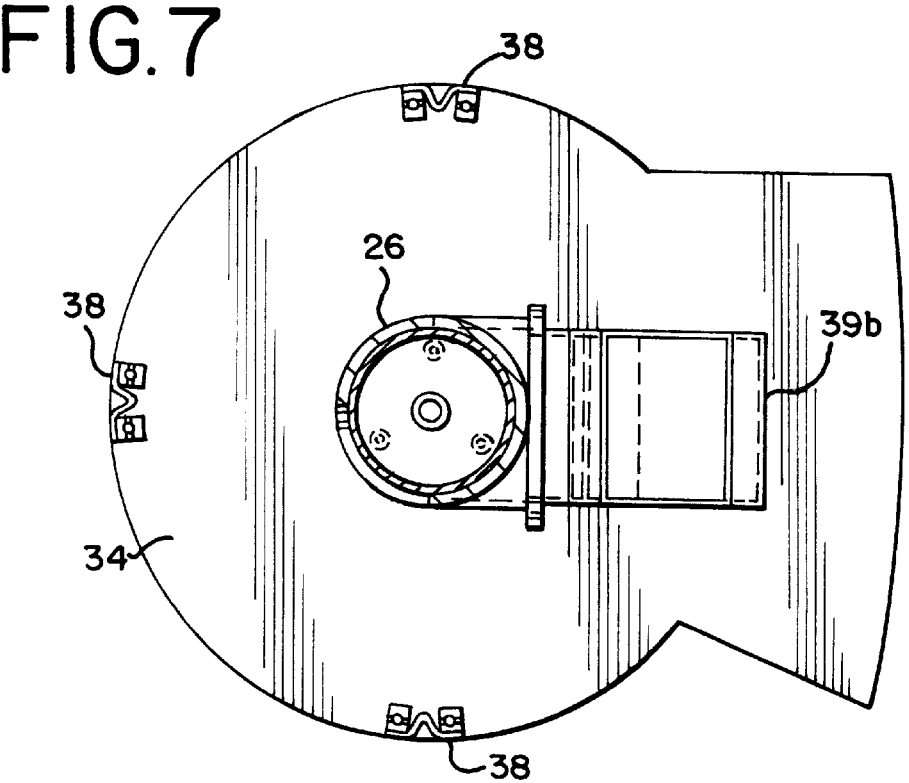
FIG. 7 is a cross-sectional view of the apparatus of FIG. 5, taken along 6—6.

As set forth above and shown in FIG. 2, light box includes cylindrical tube 28, attached to the top of platform 36 of base assembly 23. As shown in FIG. 6, to prevent undue heating of the fluid being treated, tube 28 separates the interior of light box 10 into a light source region 40 and a fluid treatment region 42 between the tube 28 and the housing 12. As shown in FIG. 2, tube 28 encloses light source 24 and retractable shutter 26. Tube 28 is made of any material substantially transparent to the light emitted by the light source and should be made of a material that is heat tolerant. Suitable materials with good light transmission and thermal properties include many of the acrylic polymers, although other materials may also be used. In addition, the interior (or exterior) surface of tube 28 may be made of or coated with a material that is translucent to the desired wavelengths but reflective or opaque to undesired wavelengths. For example, the surface of tube 28 may include a material that removes ultraviolet (UV) or other light that is unnecessary for activation of the photochemical agent. Also, the surface of tube 28 may include a material that removes infrared light which would otherwise create undesired heat (that will heat the biological fluid). Such a material includes a film consisting of a PET substrate onto which metallic layers are sputtered. Such a film is marketed by Southwall Technologies under the name Altair ALT-M-20. For mounting and rotating the carriage 30, the top of tube 28 includes a motor and carriage mounting plate 44, as shown in FIG. 2. The mounting plate 44 is largely open to allow heat generated within the light source region 40 to exit out the top of tube 28 (and through a vent in the housing).

As shown in FIGS. 2 and 3, drive motor is suspended from the mounting plate 44. The shaft of the drive motor extends through plate 44 and is attached to an upper frame piece of the carriage 30 to rotate the carriage about its central axis 48. Motor 46 is connected to a power supply via connection wires (not shown). Alternatively, motor 46 may be located elsewhere. In another embodiment, motor 46 may be located, for example, between base plate 34 and platform 36 and the carriage may be mounted on a large bearing ring on the platform 36 for rotation about the light source. The motor, in this embodiment, could drive the carriage via gears or drive belts as one skilled in the art would understand.

Regardless of where the motor 46 is located, motor 46 should be of the type that allows for precise control of the motor functions and, more specifically, allows for incremental rotation of carriage assembly 30. One example of such motors are step motors. Step motors are well known to those of ordinary skill in the art and available from manufacturers such as Applied Motion Products of Watsonville, Calif.

For holding bags of biological fluid, such as blood plasma, the carriage, generally at 30, is located within housing 12. As shown in FIGS. 2–5, carriage 30 includes a top bracket 25a and a bottom bracket 25b and vertical framing 25c therebetween, to form a generally cylindrical framework for supporting bags of biological fluid to be treated. As best seen in FIG. 2, brackets 25a and 25b are hexagonal, providing a hexagonal cylindrical framework, with each side of the hexagon defining a bag receiving area on the framework. Of course, carriage assembly 30 including its top bracket 25a, bottom bracket 25b and vertical framing 25c may form other regular polygonal structures to accommodate a different number of containers. (For example, the cylindrical framework may be triangular, octagonal or other shape).

As best seen in FIGS. 3a–3d and 4–5, the top bracket 25a includes hooks 50 for suspending plastic containers or bags of biological fluid such as blood plasma or other blood components. A hook 50 is located at each of the hexagonal sides of the carriage, allowing flexible plastic containers 32 (shown in FIGS. 3—3 (a–d) of a biological fluid such as blood plasma to be hung within the bag receiving area. A pair of fixed vertical bars 52 extend between top and bottom brackets 25a and 25b in each bag receiving area to provide inner rests, against which the container 32 of biological fluid may be pressed to distribute the fluid more evenly within the container for treatment. In this regard, each bag receiving area of carriage 30 includes a bag holder 54 for compressing the bag to more evenly distribute fluid for treatment. The bagholder 54 includes a wire frame, hinged to the bottom bracket 25b for opening and closing. The top of each bag receiving area (above hook 50) includes a latch 56 for holding the holder 54 in a closed position.

Thus, as shown in FIGS. 3a–3d, when a plastic container 32 filled with biological fluid is hung from hook 50, and holder 54 is placed over the container and locked into position, horizontal bar 58 of holder 40 presses the fluid (which tends to aggregate in the lower half of container 32 due to gravity) against the inner vertical inner bars, and thus more evenly distributes the biological fluid throughout container 32.

Container 32 is made of any translucent material that is suitable for storing a biological fluid, such as blood or blood components and a photochemical agent. Preferably, the container 32 is made of a plastic such as a polymeric material or a polymeric blend. Containers useful in the present invention are described in U.S. Pat. No. 5,514,106, which is incorporated by reference, U.S. patent application Ser. No. 08/121,820, also incorporated by reference and/or U.S. patent application Ser. No. 08/742,572 entitled "Systems and Methods for Removing Viral Agents from Blood" in the name of Robert Herman, John Chapman, Sun Chong-Sun, Jean M. Mathias, Veronique Mayadoun, Serge Degheidere and Daniel Bischof, filed on Oct. 28, 1996 also incorporated by reference herein.

The specific carriage shown in FIG. 2 can accommodate up to six containers (one container within each compartment) of biological fluid. Of course, it should be understood that carriage 30 can have as many or as few bag receiving areas as possible and/or necessary. In fact, carriage 30 can be removed from platform 36 and replaced with a carriage capable of holding, for example, three larger containers or more (e.g. 8) smaller containers.

As shown in FIGS. 4–6, carriage 30 also includes wedged or V-shaped reflectors 60 along vertical members 25c and spaced between each of the bag receiving areas for reflecting light from light source 24 (and that has been transmitted through containers 32). As best shown in FIG. 6, surfaces 62 of reflectors 60 are angled toward the interior of light box 10 and, more specifically, with the vertex of the wedge aligned toward light source 24. The surface 62 of reflector 60 may be a composite of two or more angles or may be a generally smooth concave surface. Reflectors 60 and, more particularly, surfaces 62 may be coated, covered or made of any highly reflective material that, does not significantly diminish the intensity of the light and/or light energy reflected back onto containers. One such material is known by its tradename Everbrite 95 sold by Alcoa Brite products. Everbrite 95 includes a highly reflective layer of silver sputtered on a layer of polyethylene terephthalate (PET) film. The treated PET film is then bonded to an aluminum or steel substrate.

As described above, carriage assembly 30 is enclosed by housing 12. The interior surface 64 of housing 12 (shown in FIG. 2) is also coated, covered or made of a highly reflective surface similar or identical to the material used for reflectors 60 as described above. Having the interior surface made of a highly reflective surface allows light from light source 24 (and transmitted through container 32) to be reflected back onto the container. The highly reflective nature of the inner surfaces reflects light back at the containers with minimum reduction in its intensity. This helps to provide for substantially uniform exposure of the fluid, as well as uniform illumination from container to a container.

Finally, light box 10 includes fans 39a and 39b. Fan 39b blows cool air through the tube 28 and the into light source region to cool light source 24. Fan 39a blows cool air through fluid treatment region 42 to prevent undue heating of the containers 32, as they are rotated by carriage 30.

Figure 8:
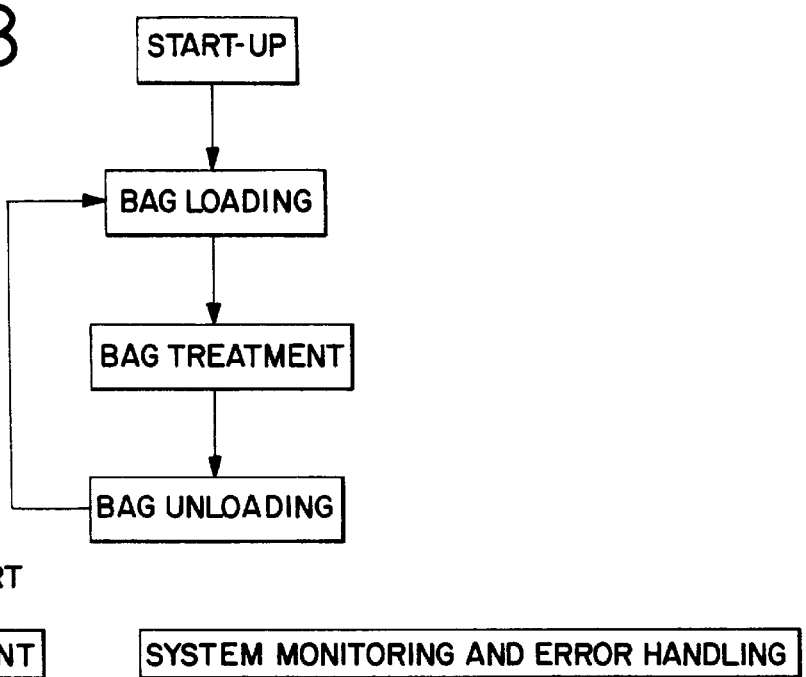
FIG. 8 is a flow chart showing the control system for the present invention.
Figure 9:
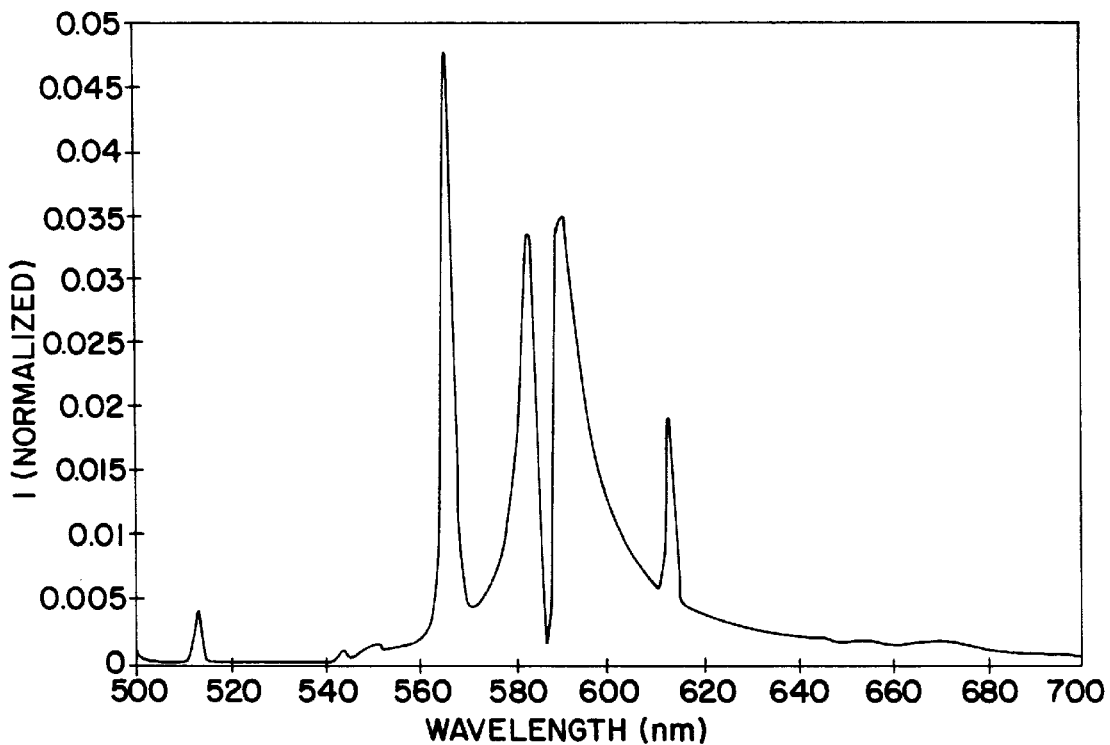
FIG. 9 is a graph showing the normalized spectral distribution of high pressure sodium light between 500–700 nm.

A programmable computer-based control system, depicted generally and diagrammatically in FIG. 8, may be used to control the operation of the light box 10. As shown in FIG. 8, the system tests, monitors and controls various aspects of the light box operation such as the start-up, container loading, container treatment and container unloading stages of the light box operation. The various stages may be initiated by the operator through control panel 20 or automatically by the control system. For example, during the "start-up" phase, the control system tests the operation of the light source to determine whether it is functioning properly. As part of the check of the light source 24, control system activates light source 24, raises shutter 26 and, after a warm up period, measures the energy generated by the light source. (Alternatively, the energy generated by the light source may be measured with shutter 26 lowered). If the energy is within a range acceptable for treatment of the biological fluid, light source 24 is turned off and shutter 26 is lowered. (Alternatively, light source may remain on and be covered by shutter 26 until the time of the container treatment phase.) Based on the light energy readings, an estimated treatment time may be calculated by the control system. If the control system determines that the light box components are functioning properly, the operator may instruct the control system (or the control system may do so automatically) to proceed to the "Container Loading" phase of the system operation.

During the Container Loading phase, the control system determines the carriage type and the number of bags to be processed. During loading of the containers, carriage 30 may be automatically advanced to allow for balanced loading of the carriage. For example, if carriage is designed to hold 6 containers, the carriage will advance in such a way as to evenly distribute the containers 32 around the carriage 30. Thus, if for example, only 4 containers are to be treated on a carriage capable of holding six containers, the carriage will allow for placement of the first container in a first position and will then automatically advance to a position directly opposite the first position. The carriage will then allow for loading of the third container and advance to a position directly opposite the third container for loading the fourth container. Balancing the carriage as described above makes it more likely that during the illumination cycle each of the containers will receive a substantially uniform quantity of light and none of the containers will be substantially blocked from the light by adjacent containers. It also reduces undue wear on the motor and bearings due to unbalanced loads.

In addition, during the Container Loading phase, the system may also check and record the particulars of the container and, if the biological fluid is blood or a blood component, check that the blood or blood component is appropriate for treatment (e.g. that the component is blood plasma). For example, the containers may include bar codes or other identifiers that identify the product codes and lot numbers of the container and other specifics about the blood donation (e.g. type of component). If the control system recognizes an invalid code, lot number or other defect, it marks the container and/or alerts the operator.

After the Container Loading phase, the operator may instruct the system to proceed to the next phase, the Container Treatment phase. During the Container treatment phase, the instrument again goes through a sequence of tests to ensure that its component parts, such as the light source, are functioning properly. If the light source has been turned off (after the start-up phase), the light source is activated and allowed to reach its required intensity before shutter 26 is lowered. This prevents containers 32 from being exposed to a light that has not reached its desired intensity and that may be spectrally unstable or undesirable.

Light box 10 includes, as part of its control system, sensors 66 and 68 for monitoring the amount of light being emitted by the light source 24 and the amount of light transmitted through the biological fluid in containers 32. As shown in FIG. 2, sensor 66 may be located on or near cylinder 28 and measures and monitors the amount of light contacting the biological fluid directly from the light source 24. A second sensor 68 may be placed on or near the interior surface of the housing 12 to measure and monitor the amount of light transmitted through the biological fluid for reflection back onto containers 32. Alternatively, the control system may utilize one sensor as the primary sensor and a second sensor as a back up or check. In another embodiment, control system may monitor the treatment of the biological fluid by measuring the amount of time the biological fluid is exposed to the light from the light source and calculating the amount of energy received by the biological fluid. Also, the control system may monitor the treatment of the biological fluid in each container on a container per container basis, or may monitor the entire treatment process and arrive at an average treatment profile for the containers.

The control system may be preprogrammed to determine if the amount of light emitted directly by the light source and transmitted through containers 32 is sufficient to effectively treat the biological fluid. Thus, if the light box is being used to inactivate virus in blood or a blood component with a photochemical agent, the control system may be preprogrammed to determine if the amount of light is within the range required to activate the photochemical agent or, in other words, to inactivate the contaminants.

For example, if the biological fluid is blood plasma and the photochemical agent is methylene blue, the control system may be preprogrammed to determine whether the light energy contacting the container (from both sides) is within the intended exposure range. If sensors 66 and 68 determine that one or more of the containers has not been sufficiently illuminated, the treatment time may be extended to ensure that the deficient container receives additional treatment, but without overexposing the remaining containers that may be within the preferred intensity range. If providing further treatment to the deficient container would result in overexposure of the remaining containers, no further treatment will be provided and the control system will mark the deficient container or otherwise alert the operator that the deficient container has not been sufficiently treated.

Light box 10 described above may be used for treating any fluids with light, but is particularly useful in the treatment of blood or other biological fluids with light and, more specifically, for the viral inactivation of blood and blood components.

Light box 10 allows for multiple containers or units of biological fluid to be treated at the same time. This results in lower cost per unit treated. The ability to treat several containers or units of biological fluid provides a savings to the treatment center, as fewer instruments for treating a given amount of biological fluid will be required. Light box 10 is fairly compact (approximately 32 inches high×30 inches wide by 18 inches) thus, requiring less space and making it more convenient to place in different locations.

Although the operation of the light box 10 will be described in the context of treating blood with light for the purpose of inactivating viruses in the blood, it is to be understood that the invention is not limited to the specific example described below, nor is it limited to viral inactivation of blood or blood components.

In accordance with the method of treating a biological fluid with light, containers 32 of biological fluid containing a photochemical agent and contaminants are placed on carriage 30 of the light box 10. As used herein, contaminants refers to any harmful biological material, and particularly includes bacteria, parasites and viruses. As described above, containers 32 may be hung from hooks 50 of carriage 30 and secured by bag holder 54. During placement of containers 32 and during activation of the light source, it is desirable that retractable shutter 26 be in the closed position to shield the operator and the containers 32 from the light source before it has reached its desired intensity. Shielding the containers from the light source as it is being activated and as the containers are placed on the carriage is another way to ensure uniform treatment of the containers by preventing some of the containers from receiving some light before the others have been placed on the carriage. The shutter also shields the containers from a light source that might be spectrally unstable. A spectrally unstable light source may cause erroneous readings in the useful (i.e. energy in the absorption band of the photochemical agent) energy received at the container. Once the light source has reached its desired intensity, the retractable shutter 26 is lowered and the containers 32 are exposed to light.

Carriage 30 is rotated around its central axis 48. for a predetermined period of time. In accordance with the present invention, the typical time of exposure of the biological fluid may be anywhere between 0.3 and 30 minutes or, more preferably 1 to 5 minutes. The time of exposure will depend on the amount of light energy contacting the containers, and the fluid therein. As described above, if the fluid to be treated is blood plasma and the photochemical agent is methylene blue combined in the ratios below, it is desirable that the containers 32 of blood plasma be treated with energy in the range of 17–31 Joules/cm$^2$ of light in the wavelength range corresponding to the absorption band of the photochemical agent (e.g. for methylene blue the corresponding wavelength would be 550–700 nm). If any one container has not been exposed to energy within the desired range, the procedure or treatment may be extended.

Rotation of carriage 30 also provides for uniform treatment of the biological fluid. Rotation of carriage 30 ensures that each container will be exposed to every part of the fluid treatment region 42 for similar duration. Rotation also ensures that the each container is uniformly cooled by, for example, fan 39a.

Figure 10:
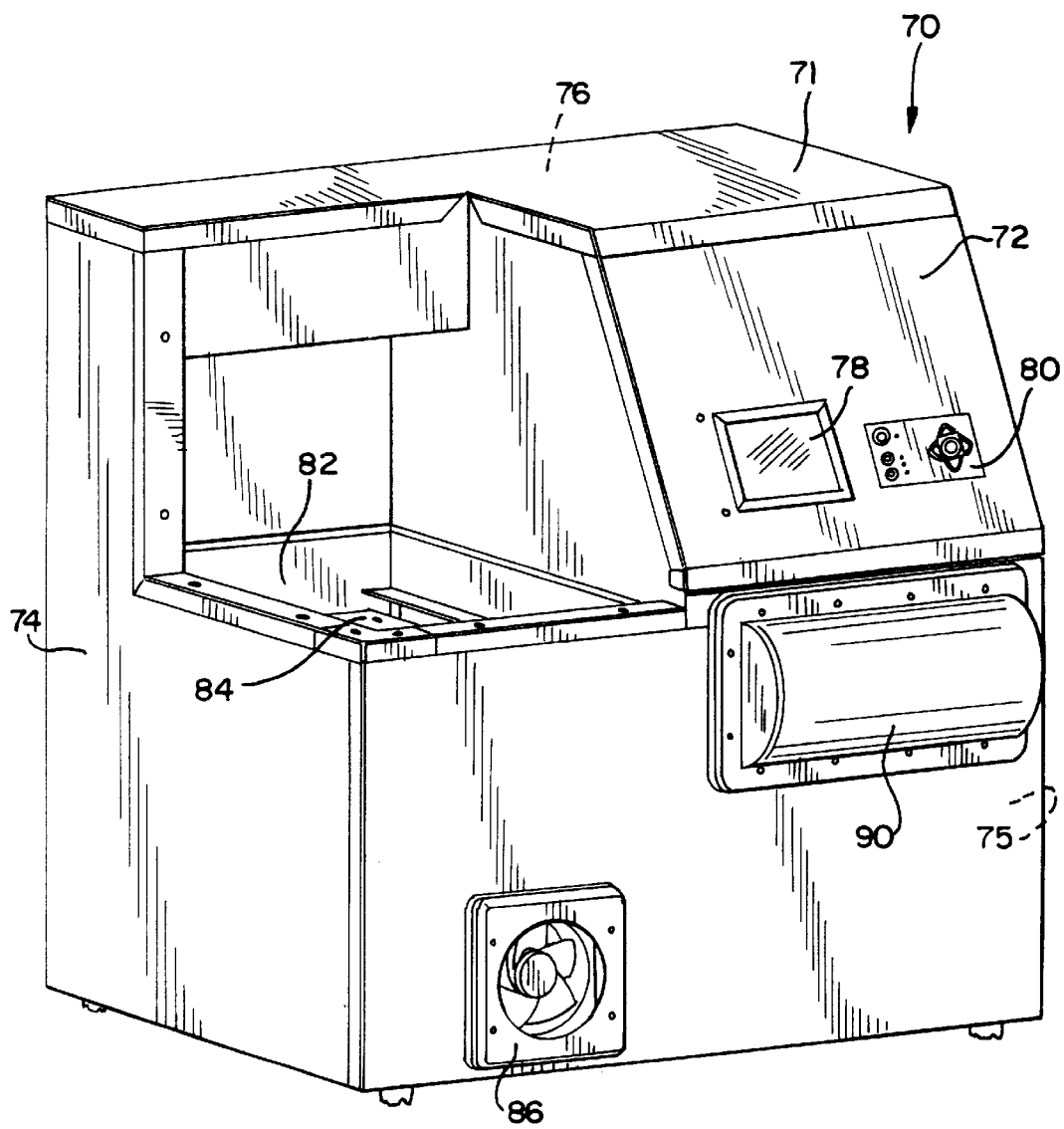
FIG. 10 is a perspective view of another apparatus embodying the present invention.

In another embodiment of the present invention, the light box may provide for direct, two sided illumination of the biological fluid. One example of such a light box is shown in FIGS. 10–16. In particular, as shown in FIG. 10, light box 70 may generally include a top panel 71, front panel 72, side panels 74 and 75 and a rear panel 76. Front panel 72 may include LCD display screen 78 and key pad 80 to allow for operator control of light box 70. Light box 70 may also include a container loading area 82 and a slidable tray subassembly 84 located (when, for example, fluid is not being treated) within loading area 82. As further seen in FIG. 10, light box 70 may include fan 86 for cooling the ballast and additional fans (shown in more detail in FIG. 11) for cooling the treatment area.

Figure 11:
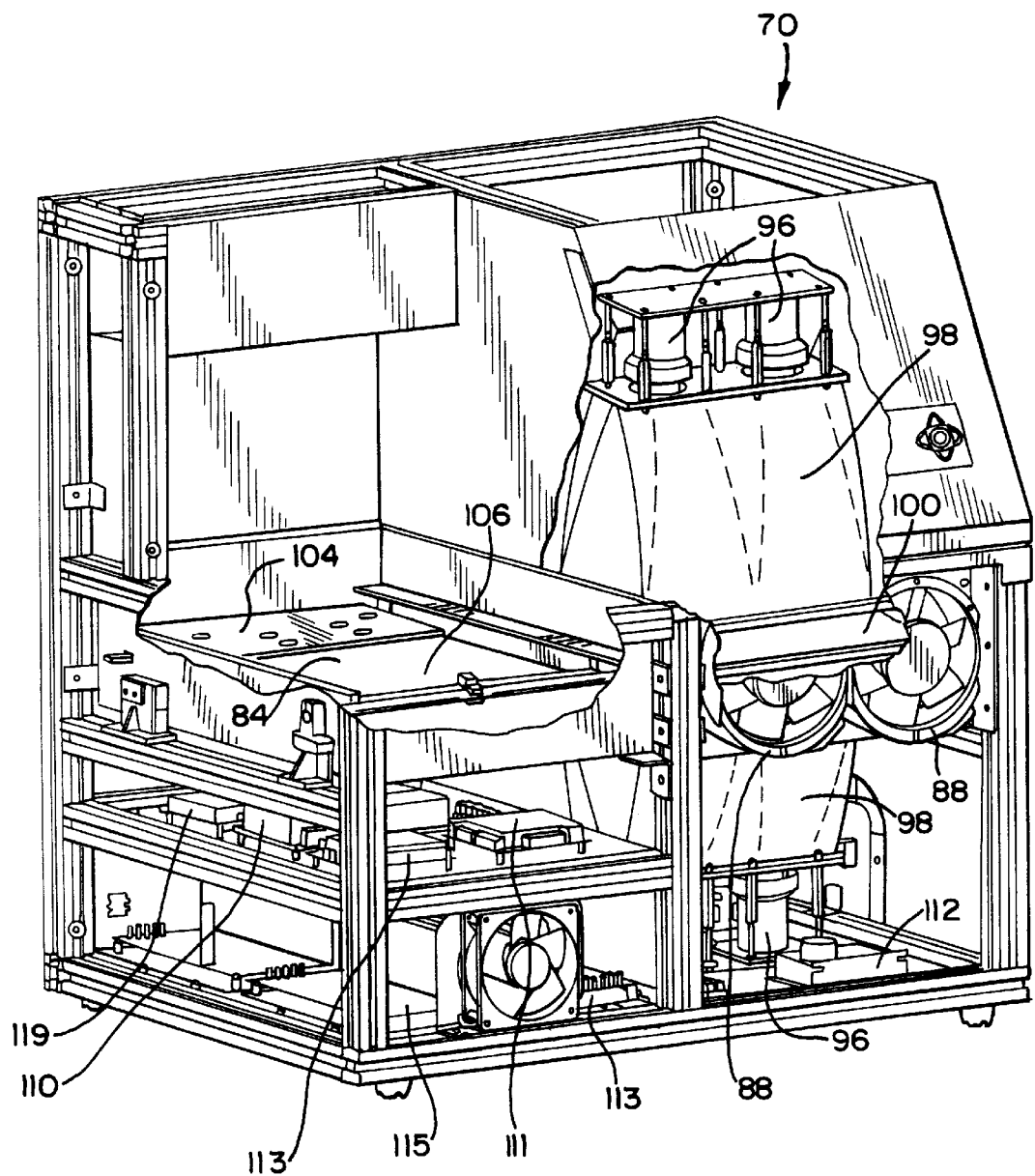
FIG. 11 is a perspective view of the apparatus of FIG. 10 with a portion of the front panel removed to show the interior of the apparatus.

Turning now specifically to FIG. 11, light box 70 may include one or more light sources or lamps 96 for illuminating containers of biological fluid. For example, one lamp or one series of lamps 96 may be disposed in the upper portion light box 70 near the top panel 71 and another lamp or series or lamps 96 may be disposed in the lower portion of light box 70. The light box 70 specifically shown in FIG. 11 includes, for example, two side-by-side lamps 96 in the upper portion of light box 70 and two side-by-side lamps 96 (only one of which can be seen) in the lower portion of light box 70. of course, it will be recognized that the number and arrangement of lamps may vary and is not limited to the arrangement shown in FIG. 11. Lamps 96 and, more specifically, the bulbs of lamps 96, are housed within reflector subassemblies 98.

Located between the reflectors subassemblies 98 is a treatment area 100 for receiving slidable tray subassembly 84 and, more specifically, containers of biological fluid loaded thereon, for illumination (treatment) by lamps 96. Tray subassembly 84 may include label stage 104 and a substantially transparent tray platform 106.

As shown in FIG. 12, tray subassembly 84 may be slidably attached to tracks 114 and 116 which extend from tray loading area 82 (shown in FIG. 11) to treatment area 100 (FIG. 11). Movement of tray subassembly is effected by rack and pinion gear 117 coupled to a motor (not shown). Alternatively, as will be appreciated by one of ordinary skill, movement of tray subassembly may be effected by a motor and drive belt arrangement, or motor and lead screw arrangement.

Reflector subassembly 98 includes frame 118 and window 120 which separates, for example, the interior chamber or cavity of reflector subassembly from treatment area 100. Reflector subassembly 98 further includes an interlocking framework of dividing walls 122 and sides 124. As seen in FIG. 13, sides 124 may include slits 126 for interlocking engagement with teeth 128 of dividing walls 122. Of course it will be appreciated that walls 124 and sides 122 may be assembled together by welding or other suitable means. In any event, when assembled, the walls 122 and sides provide discrete light chambers or cavities. As seen in FIGS. 12 and 13, the walls 122 and sides 124 are curved so that each set of walls 122 and set of sides 124 is generally in the shape of a compound parabolic curve. Stated differently, each pair of opposing walls 122 of a light chamber provides a compound parabolic curve and each pair of opposing walls 124 of a light chamber provides a compound parabolic curve. Thus, for example, in FIGS. 12 and 13, each light chamber includes interior surfaces made up of two compound parabolic curves. The compound parabolic curves of each chamber allows for uniform distribution of light from lamp 96 and maximum illumination of treatment area 100.

Continuing with the description of the reflector subassembly 98, window 120 may be made of glass, plastic acrylic polymer or any other suitable transparent material that is also heat tolerant. Additionally, window 120 may include a filter 121 or be coated (by physical vapor deposition (PVD), CVD or the like) with a material (e.g. aluminum oxide, indium tin oxide (ITO) or silicon monoxide) that filters out and/or reflects (and does not substantially transmit) unwanted infrared light. For example, in one embodiment, window 120 may be made of silica glass that has been treated by PVD. Such a material is available from Corning Incorporated of Corning, N.Y. and sold under the name Vycor(R) 7913, and treated by Thin Film Devices of Los Angeles, Calif. for near infrared (NIR) and mid infrared (MIR) reflection.

Reflector dividing walls 122 and sides 124 may be made of or coated with a highly reflective substance that does not significantly diminish the intensity of the light and/or light energy reflected onto the containers. The reflective material used for reflector subassembly 98 may be selected from any material which will maximize the amount of light delivered to treatment area 100. As set forth above, the walls 122 and sides 124 of reflector subassembly 98 may be made of a steel, aluminum or other metallic substrate that has been treated with a highly reflective material (e.g. brightened anodized aluminium on a layer PET substrate). In one embodiment, for example, the reflector walls 122 and sides 124 are made of a material sold under the trade name MIRO 1 available from ALANOD, of Ennepetal, Germany.

Light source or lamp(2) 96 should provide a high intensity light capable of providing maximum activation of a photochemical agent without significantly harming other desirable components in the biological fluid. Lamp(s) 96 should provide a high intensity light as that term is defined herein (i.e. at least 30 mw/cm$^2$.) Examples of such high intensity light sources include high pressure sodium lamps, halogen lamps, sulfur lamps, metal halide lamps, xenon lamps, lasers, laser diodes or other lamps including white fluorescent lamps. In one embodiment, lamps 96 should provide a high intensity light (i.e. at least 30 mw/cm$^2$) when measured across the range of 550–700 nm at the biological fluid and when the photochemical agent is methylene blue. High pressure sodium lamps capable of providing an intensity of between about 80–150 mw/cm$^2$ are particularly useful. In one embodiment, lamp(s) 96 are high pressure sodium vapor lamps available from Phillips Lighting of and sold under the tradename Ceramalux.

Light box 70 may also include a power supply and, as shown in FIGS. 11 and 12, control elements such as sensors, central processing unit (CPu) 110, motor driver board 112, relay board 111, display driver 113. Light box may also include ballasts 115 for controlling current to lamps 96.

Light box 70 includes a programmable, computer based control system (as generally shown in FIG. 8) that may be used to control the operation of light box 70. In particular, using sensors, internal computers and the like, the system tests, monitors and controls various aspects of light box 70 operation such as, but not limited to, the start up and container loading, treatment and unloading phases of the light box operation. The various phases may be initiated by the operator through control panel (and specifically key pad 80) or automatically by the control system without operator intervention.

For example, during the "start up" phase, the control system may test the operation of the light source. As part of the check of the light source (lamp(s) 96), the control system may activate lamp(s) 96. After a brief warm-up period (approximately 5 minutes), light sensors measure the energy provided by lamps 96. If the energy level is within a predetermined range, the system indicates that the instrument is ready to receive the containers of biological fluid. Either automatically or through a key stroke by the operator, tray subassembly 84 (with containers thereon) is moved from container loading area 82 (FIG. 10) to treatment area 100 for the "treatment phase" of the procedure. When treatment is complete (i.e. when the container(s) has been illuminated for a selected amount of time at the desired energy level) tray assembly 84 is automatically withdrawn from the treatment area 100 and returned to the loading area 82. The treated containers are then removed and the instrument is ready to receive additional containers for treatment.

The control system may also monitor the temperature of the containers. If the biological fluid within container is subjected to excessive heat, the fluid (e.g. plasma) may be unsuitable for transfusion to a patient. Accordingly, light box 70 may include a sensor (thermocouple 119) for measuring the temperature of the container before and after treatment. If the temperature of the container exceeds a predetermined value, the container may be labeled (either by the instrument itself or the operator) as unsuitable and discarded.

Figure 14:
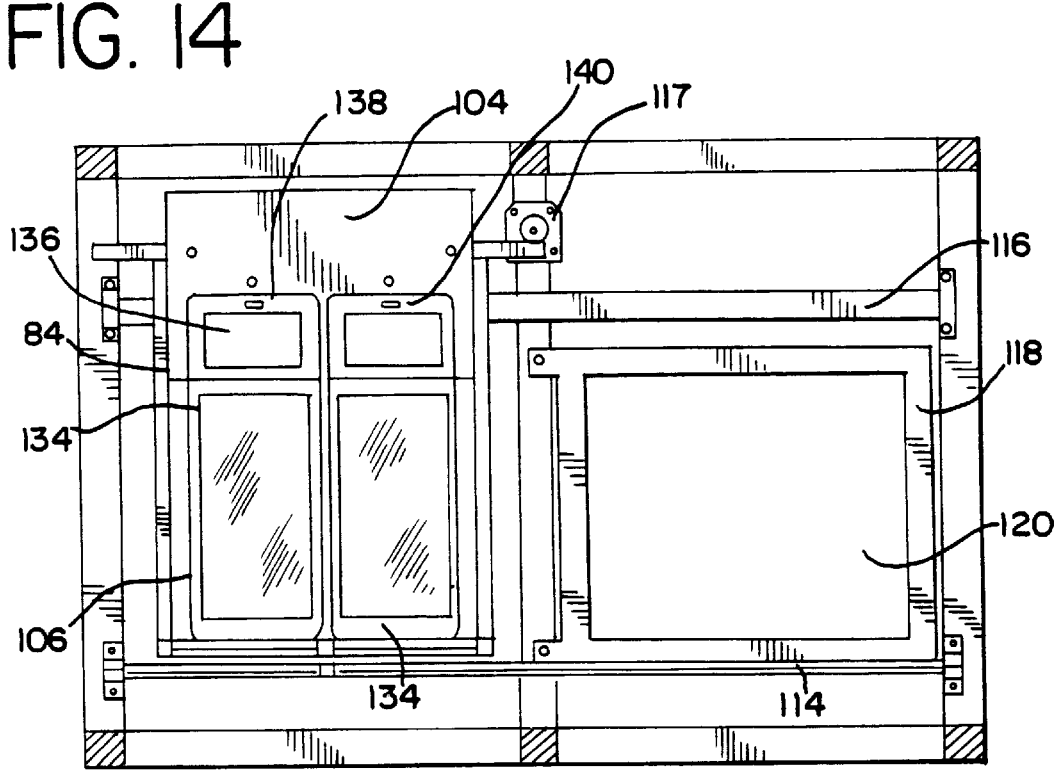
FIG. 14 is a top view of the tray subassembly and treatment area of the apparatus of FIG. 10 with containers in the loading area.
Figure 15:
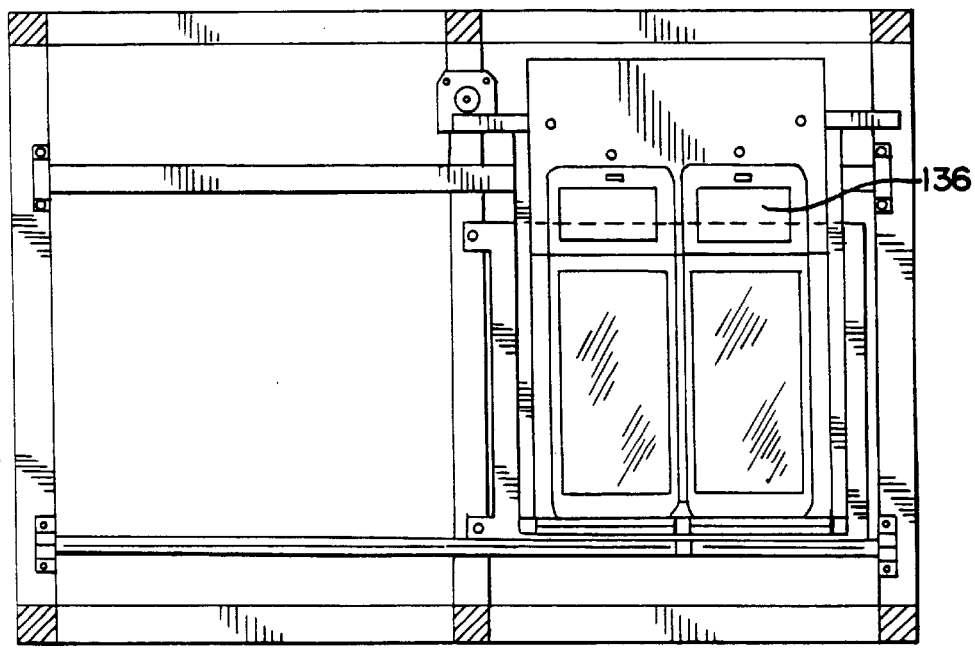
FIG. 15 is a top view of the tray subassembly and treatment area of the apparatus of FIG. 10 with containers within the treatment area.
Figure 16:
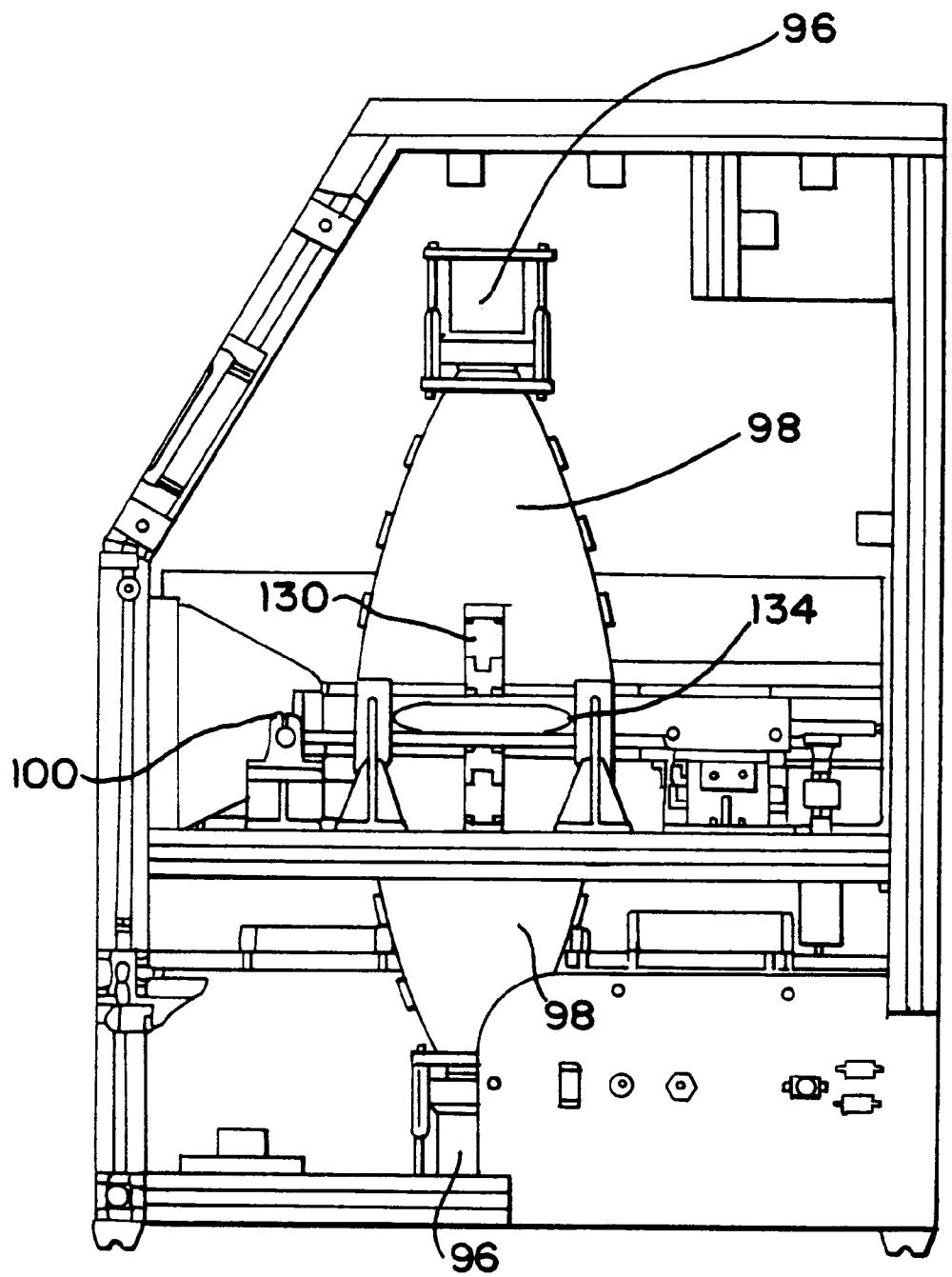
FIG. 16 is a side view of the apparatus of FIG. 10 with the side panel removed to show the interior of the apparatus and a container within the treatment area.

Turning now to a more detailed discussion of the method for treating the biological fluid in accordance with this invention, the biological fluid may be first processed through a disposable tubing set such as substantially shown and described in U.S. Ser. No. 08/742,572 (incorporated by reference) and combined with a selected amount of the photochemical agent in container 134. For example, when the photochemical agent is methylene blue, the biological fluid is combined with between approximately 90–400 μg of methylene blue in container 134. Containers 134 (as shown in FIGS. 14, 15 and 16) of a biological fluid, such as blood plasma, are placed onto tray subassembly 84. (Plasma, as typically understood, means plasma that is substantially free of RBC and/or other cellular components—for example, less than approximately 6×10$^9$ RBC, less than 0.1×10$^9$ WBC, less than 50×10$^9$ platelets per liter.) Although, two containers 134 are shown in FIGS. 14 and 15, it will be appreciated that tray subassembly 84 can accommodate one large container or two or more smaller containers. Returning now to FIG. 14, containers 134 are placed on tray subassembly 84 such that label portions 136 rest on label stage 104. Label stage 104 may, if desired, include tabs to further ensure proper placement of containers 134 on tray subassembly 84. More specifically, the holes 140 in containers 134 are placed over tabs 138 to ensure proper placement, and if desired, eliminate or minimize movement of the containers during treatment. Of course, any means for securing containers 134 on tray subassembly 84 are within the scope of the present invention. Transparent portions of container 134 rest on the transparent platform 106 of tray subassembly 84.

As described above, movement of tray subassembly 84 may be automatically controlled by the operator through key pad 80 to effect movement from loading area 84 to treatment area 100. Specifically, tray subassembly 84 moves along tracks 114 and 116 until it reaches and is positioned in treatment area 100. As shown in FIG. 16, container(s) 134 are subjected to two sided illumination from above and below treatment area 100 by lamps 96. Once the treatment is complete, tray subassembly 84 is returned to loading area from where the treated containers 134 are removed. As set forth above, treatment of the containers may be anywhere between 0.3–30 minutes and preferably between about 1 and 5 minutes.

A light sensor 130 shown, for example, in FIGS. 12 and 16 continuously reads the level of energy at or near the container and transmits its readings to a microprocessor where the measured energy is compared to a predetermined energy level (the energy level required to produce acceptable viral kill and protein recovery), such as, for example, between about 1 and 100 J/cm$^2$ and, more typically, 10–50 J/cm$^2$. If the measured energy substantially corresponds to the predetermined level, treatment is complete. A signal from the motor driver board 112 to the motor activates the motor, and tray assembly is automatically withdrawn from the treatment area.

Additional sensors are also included in light box 70. For example, light box 70 may include air flow sensors to measure the level of air flow within treatment area. If air flow within the treatment area is insufficient prior to treatment, treatment may be terminated or even precluded. A suitable temperature and air flow within treatment area are desired so that containers are not exposed to excess heat during treatment which may, in some circumstances, make the biological fluid, such as blood, unacceptable for later transfusion.

In accordance with one embodiment of the present invention, the energy measured by sensors 130 is the combined energy provided by the top and bottom lamp(s) 96. In order to provide for a more accurate reading of illumination or treatment process, the microprocessor or internal computer may provide the measurement readings in terms of the useful energy for the activation of the photochemical dye, such as methylene blue (i.e. approximately 590–690 nm). Stated differently, the measured reading of energy is not of the total energy applied, but rather the amount of useful energy (i.e. useful for activating the photochemical dye) applied at the treatment area.

In accordance with the present invention, it is believed that the use of a high intensity light with a biological fluid such as blood or blood plasma containing a selected amount of methylene blue enhances the virucidal effect of the methylene blue. As compared to a lamp that provides low intensity light to the biological fluid, it is believed that use of the high intensity light to contact the biological fluid increases the number of photons contacting the methylene blue molecule per unit of time and, if those photons are of energies corresponding to the absorption wavelengths (in free space) of methylene blue, increases the production of the singlet oxygen which causes the secondary reactions responsible for inactivating the viruses in, for example, blood plasma. In accordance with the present invention, the preferred ratio of methylene blue to blood plasma is between about 1:20 to 1:35, but may be 1:200 to 1:350. Thus, approximately 1–10 ml of methylene blue may be used when the volume of plasma is generally between 200 and 350 ml, and preferably between 260–340 ml. The concentration of methylene blue can be approximately between 1 to 10 $\mu$M and, preferably, approximately 1 $\mu$M or more preferably 2–4 $\mu$M.

As set forth above, methylene blue is activated by light having wavelengths of between approximately 550 and 700 nm (typically 590–690 nm) with a peak at 663 nm. Absorbance of light in this range is understood to provide for activation of methylene blue without any significant negative effect on plasma or plasma proteins (which absorb light primarily between 300 to 560 nm). In addition, for maximum virucidal effect in a short period of time, the light intensity should be greater than 30 mW/cm$^2$ at the biological fluid or container thereof, and preferably between 80–150 mW/cm$^2$ measured at the biological fluid (or container thereof) and in the wavelength range from 550–700 nm. The typical dose of energy provided may be between 1 and 100 J/Cm$^2$, more typically between 1–50 J/cm$^2$, with doses between approximately 10–50 J/cm$^2$ being preferred and 35–45 J/cm$^2$ being most preferred.

EXAMPLE 1

In one example, units of fresh frozen plasma spiked with pseudorabies virus (PRV) were processed through a leuko-reduction filter and illuminated with a high pressure sodium light in a prototype light box similar in substantial respects to light box 10 shown in FIGS. 1–8. In one experiment, a single pack of plasma including 310 ml and plasma spiked with PRV (1:10 spike) and 10 ml of methylene blue was irradiated with the high pressure sodium light having an intensity of approximately 119 mW/cm$^2$ when measured in the absorption range of 550–700 (which corresponds to 137 mW/cm$^2$ when measured across the band of approximately 350–800 nm) for up to eight minutes. Levels of virus were measured at 0.5, 1.0, 2.0, 4.0 and 8.0 minute intervals using the conventional plaque assay. In addition, levels of virus in 5 ml aliquots were also measured at the above time intervals.

In addition to the above, a separate experiment involving one container of spiked PRV plasma and methylene blue (as described above) was treated with five containers of plasma (unspiked) in light box 10 shown in FIGS. 1–8. The light intensity applied was 115 mW/cm$^2$ when measured in the absorption range of 550–700 (which corresponds to 133 mW/cm$^2$ when measured across the band of approximately 350–800) and samples were taken at the above time intervals. Levels of virus were measured in accordance with the conventional plague assay and in 5 ml aliquots. The results of these experiments are set forth in Table 1.

TABLE 1

Comparison of Methylene Blue viral inactivation of a single container of methylene blue plasma with multiple (6) containers of methylene blue plasma

| | | Virus titer (Log PFU/ml) | | Virus titer (Log PFU/5 ml) | |
|---|---|---|---|---|---|
| Sample | Dosage* | single pack | multiple pack | single pack | multiple pack |
| process control | 0 J/cm2 | 4.9 | 5.1 | | |
| 0 min | 0 J/cm2 | 4.7 | 4.8 | | |
| 0.5 min | 4 J/cm2 | 1.3 | 2.2 | | |
| 1 min | 8 J/cm2 | <0 | <0 | 1 | 2 |
| 2 min | 16 J/cm2 | <0 | <0 | 0 | 0 |
| 4 min | 32 J/cm2 | <0 | <0 | 0 | 0 |
| 8 min | 64 J/cm2 | <0 | <0 | 0 | 0 |

*as measured in the range of approximately 350–800 nm.

TABLE 2

| Sodium Light (140 mW/cm²) Light Dose* with HPS J/cm² (min) | Virus Titer in PFU/ml (LRV) | White Fluorescent Light (24 mW/cm²) Light Dose with White Fluorescent Light in J/cm² (min) | Virus Titer in PFU/ml (LRV) |
|---|---|---|---|
| 0 | $1.6 \times 10^6$ (baseline) | 0 | $5.6 \times 10^5$ (baseline) |
| 2 (0.25 min) | $1.1 \times 10^5$ (1.2) | 1 (0.9 min) | $3.1 \times 10^5$ (0.3) |
| 8 (1 min) | 8 (5.3) | 5 (4.5 min) | $1.1 \times 10^4$ (1.8) |
| 16 (2 min) | <1 (>6.2) | 15 (13.5 min) | $1.0 \times 10^1$ (4.8) |
| 32 (4 min) | <1 (>6.2) | 30 (27 min) | 1 (5.8) |

TABLE 3

| Light Source | mW/cm² | minutes of light exposure | >5 Log Challenge with Pseudorabies virus | % Fibrinogen Activity Recovered |
|---|---|---|---|---|
| white light fluorescent | 8.8 | 30 | Recoverable Virus (incomplete kill) | 81% |
| high pressure sodium | 121 | 2 | No recoverable virus (complete kill) | 88% |

As shown in Table 1, using the conventional plaque assay, a minimal amount of infectious virus was recovered from plasma at one minute of illumination. No recoverable virus was identified in samples exposed to more than 2 minutes of illumination. Thus, it can be said that exposure of blood plasma, contaminated with virus and treated with methylene blue and a high intensity light, results in complete viral inactivation in a short period of time (e.g. approximately 2 minutes). Also, use of more than one container at a time does not significantly affect the level of viral kill.

The apparatus and method of the present invention also provides more effective viral kill as compared to other apparatus or methods that can provide the same or similar amount of energy (often expressed in Joules/cm² or J/cm²). Energy is the product of light intensity time and area. However, as used herein, energy also refers to energy flux (energy per unit area) because, in the present application, area is typically a fixed parameter. In accordance with the present invention, it has been discovered that increasing the intensity results in a greater biological effect (such as viral kill and/or recovery of therapeutic protein) than does an increase in the time of exposure. Stated differently, a greater biological effect is obtained at an energy level where the intensity has been increased than at substantially the same energy level where the time of exposure has been increased.

EXAMPLE 2

Units of blood plasma (approximately 300–310 ml per unit) were spiked with pseudorabies virus to achieve an approximate final virus load of $6 \times 10^5$ PFU/ml. The plasma units were processed through a disposable tubing set as generally described in U.S. Ser. No. 08/742,572 (incorporated by reference herein). More specifically, the plasma units were filtered to remove leukocytes and collected into treatment containers containing 10 ml of methylene blue in each container. The plasma with methylene blue was illuminated with a high pressure sodium light providing an intensity of approximately 120 mW/cm² as measured at the container in the absorption range of 550–700 nm (which corresponds to 140 mW/cm² at the biological fluid or container thereof when measured across the band of approximately 350–800 nm). Using the conventional plaque assay, the amount of remaining virus was measured at different energy levels. The results are shown in Table 2.

Another batch of plasma units (approximately 300–315 ml per unit) were also spiked with pseudorabies virus to achieve an approximate final virus load of $1 \times 10^6$ PFU/ml. These units of plasma were filtered to remove leukocytes and collected into similar treatment containers containing 10 ml of methylene blue in each bag to achieve 1 $\mu$M concentration. The plasma units with methylene blue were illuminated with a white fluorescent light providing an intensity of approximately 24 mw/cm² at the container when measured across the band of 350–800 nm). Using the conventional plaque assay, the amount of remaining virus was measured at different energy levels. The results are shown in Table 2.

As seen in Table 2, the intensities and doses were measured in the range from 350–800 nm. If these intensities and doses were measured over the absorption spectrum of methylene blue (550–700), the intensity for sodium light would be 121 mW/cm² and the doses would be, from top to bottom of the left hand column, 0, 1.7, 7, 14 and 28. Similarly, for white fluorescent light the intensity would be 12 mW/cm² and the doses would be, from top to bottom of column 3, 0, 0.5, 2.5, 7.5 and 15.

Thus, as shown in Table 2 with the white fluorescent light at an energy level of approximately 7.5 J/cm² as measured at the container in the absorption range of 550–700 nm (which corresponds to approximately 15 Joules/cm² when measured across the band of approximately 350–800 nm), the log reduction of virus (LRV) was approximately 4.8 as compared to greater than 6.2 logs at an energy level of approximately 14 J/cm² as measured at the container in the absorption range of 550–700 nm (which corresponds to 16 J/cm² when measured across the band of approximately 350–800 nm) with the high pressure sodium light.

EXAMPLE 3

The apparatus and method of the present invention may also allow for less damage to the therapeutic proteins. For example, samples of approximately 235 ml with approximately 10 ml of methylene blue (to obtain a concentration of approximately 1.1 $\mu$M) were prepared. One sample was treated with white fluorescent light providing an intensity at the container of 8.8 mW/cm² when measured in the absorption range of 550 nm–700 nm, and the other sample was treated with a high pressure sodium light providing a n in t ensity at the container of 121 mW/cm² when measured in the wavelength range of 550 nm–700 nm. As shown in Table 3, after approximately 2 minutes of exposure to the high pressure sodium light, no recoverable virus was detected and the recovery of fibrinogen was approximately 88%. In contrast, the sample contacted with white fluorescent light after 30 minutes of exposure did not provide complete viral kill and resulted in approximately 81% fibrinogen recovery.

EXAMPLE 4

In another example, using a light box similar in substantial respects to the sodium light box 70 shown generally in FIGS. 10–16 and a disposable tubing set as substantially described in U.S. Ser. No. 08/742,572 (incorporated by reference), units of plasma containing virus were prepared and treated. The procedure for preparing the plasma samples is described below and the results are reported in Tables 4 and 5.

Specifically, four (4) pools of plasma A, B, C, and D were prepared from units of fresh frozen plasma. Pool 1 contained approximately 310 mls of plasma (318 grams of plasma), pool 2 contained approximately 310 mls of plasma (320 grams of plasma), pool 3 contained 260 mls of plasma (267 grams of plasma) and pool 4 contained 260 mls of plasma (267 grams of plasma). Approximately 6 mls of thawed pseuodorabies virus were added to each pool to obtain approximately $1 \times 10^{5-6}$ level of virus. A 6 ml aliquot was collected from each sample to serve as a control.

The virus-spiked plasma was filtered to remove leukocytes and combined in a plastic container with approximately 10 mls of methylene blue dye to attain an approximately 1.1 $\mu$M concentration of methylene blue. Each unit of spiked plasma with methylene blue was allowed to incubate for a period of between 10 and 15 minutes. Following incubation, each container was subjected to treatment with a high intensity light in a light box similar in all substantial respects to light box 70 (using 200W sodium lamps above and below the treatment area and including an infrared removing film) described above. Containers were illuminated for approximately 80–90 seconds at an energy dose of approximately 20 J/cm² measured across the absorption range of 590 to 690 nm. A 6 ml sample of the light treated plasma was taken. Illumination continued until the total light dosage of 75 J/cm² (measured across the absorption range of 590–690 nm) was attained. A ten (10) ml sample of the further treated plasma was taken. The treated samples were than titrated by plaque assay to determine the level of remaining virus. The results are reported in Tables 4 and 5.

TABLE 4

Inactivation of pseudorabies virus by MB treatment: photoactivation by sodium light device

| | Virus titer (Log PFU/ml) | | | |
|---|---|---|---|---|
| Sample | Pool #1 | Pool #2 | Pool #3 | Pool #4 |
| Process control | 6.18 | 5.63 | 5.91 | 6.00 |
| 20 J/cm2 | <1.0 | <1.0 | <1.0 | <1.0 |
| 75 J/cm2 | <0.0 | <0.0 | <0.0 | <0.0 |

As seen in Table 4, the level of remaining virus was than 1 log after illumination at 20 J/cm² and no remaining virus could be detected after treatment at 75 J/cm².

EXAMPLE 5

In another example, two pools of fresh frozen plasma were prepared (pools #1 and 2). Each pool was divided into two units of plasma having approximately 260 ml and 310 ml of plasma respectively. Each unit of plasma was prepared and spiked with pseudorabies virus (PRV) and further processed as generally described in Example 4 to achieve approximately a 1.1 $\mu$M concentration of methylene blue. The containers of plasma were treated with energy doses of 5 J/cm², 20 J/cm² and 75 J/cm² in a light box similar in substantial respects to light box 70 (using 200W sodium lamps above and below the treatment area and including infrared film) described above. Samples were taken at each of the above-described doses and the treated samples were then titrated by plaque assay. The results are reported in Table 5 which shows no remaining virus after treatment at 75 J/cm².

TABLE 5

Inactivation of pseudorabies virus by MB treatment: photoactivation by sodium light device

| | Virus titer (Log PFU/ml) | | | |
|---|---|---|---|---|
| Sample | Pool #1 (260 ml) | Pool #1 (310 ml) | Pool #2 (260 ml) | Pool #2 (310 ml) |
| Process control | 6.44 | 6.44 | 5.86 | 5.86 |
| 5 J/cm2 | 3.93 | 4.69 | 3.87 | 4.48 |
| 20 J/cm2 | <0.5 | <0.5 | 0.37 | 0.94 |
| 75 J/cm2 | <0.0 | <0.0 | <0.0 | <0.0 |

As described above, the method and apparatus of the present invention are capable of providing a high intensity light that maximizes viral inactivation while allowing for substantial recovery of plasma proteins. Experiments were conducted to demonstrate the effectiveness of the present invention in recovering plasma proteins. The procedures, tests and results are described below.

EXAMPLE 6

Four(4) to five(5) units of ABO compatible fresh frozen plasma where placed in a 37±2° C. water bath until the plasma had completely thawed. Each unit of plasma was then sequentially sterilely connected to a 3,000 ml Viaflex® container using a Terumo® SCD 312 Sterile Connect Device, and all of the plasma was transferred to the Viaflex® container resulting in Pool A. Additional pools B-H were prepared in similar fashion.

The Viaflex® container was then sterile connected to transfer packs to which approximately 260 ml of plasma was transferred.

Each of the plasma packs were then processed as described above and filtered to remove leukocytes and collected into similar treatment containers containing approximately 10 ml of methylene blue in each bag to achieve approximately a 1.1 $\mu$M) concentration of methylene blue. The plasma units with methylene blue were illuminated for approximately 2.6 minutes with sodium light (in a light box similar in substantial respects to light box 70 described above) providing an energy of approximately 60 J/cm² measured across the wavelength of 590 to 690 nm. For comparison, similarly prepared packs of plasma with comparable concentrations of methylene blue were illuminated with a white fluorescent light for approximately 25 minutes at an energy level of approximately 48 J/cm². After illumination, 4 ml samples were taken from the packs, placed in polypropylene tubes and tested for coagulation properties and recovery of plasma proteins. Specifically, the samples were tested for Prothrombin Time (PT), (an assay for identifying coagulation abnormalities of the extrinsic and common pathways and fibrinogen), Activated Partial Thromboplastin Time (APTT) (an assay for identifying coagulation abnormalities of the contact phase and the intrinsic and common pathways of plasma activation), and Thrombin Time Assay (TT) (an assay for measuring the time taken by exogenously added thrombin to proteolyze plasma fibrinogen and to form a clot). Also, the samples were tested for recovery of the following plasma proteins: Factor II (F II), Factor V (F V), Factor VII (F VII), Factor VIII (F VIII), Factor IX (F IX), Factor X (F X),Factor XI (F XI), Factor XII (F XII), Factor XIII (F XIII), Von Willebrand's Factor (VWF), Fibrinogen (Fib), Antithrombin III (AT III), Protein C (Prot C) and Protein S (Prot S). The results are reported in Table 6.

As seen from Table 6, treatment with high intensity sodium light for a significantly shorter period of time (than, for example, white flourescent light) provided comparable, if not better, recovery of proteins.

TABLE 7

Protein Recovery in Plasma Treated with High Intensity Sodium Light (Mean Values)

| Joules | FIB(%) | FXI(%) | FVIII(%) |
|---|---|---|---|
| 0 | 100 | 100 | 100 |
| 40 | 74.0 ± 5.0 | 67.3 ± 2.89 | 80.3 ± 4.51 |
| 60 | 64.3 ± 3.06 | 64.3 ± 3.06 | 73.0 ± 3.61 |
| 80 | 60.3 ± 2.08 | 63.3 ± 2.31 | 65.0 ± 2.64 |
| 100 | 61.7 ± 2.52 | 61.0 ± 1.73 | 59.7 ± 6.43 |

Additional experiments were conducted to examine the effect of concentration of the photochemical agent on viral inactivation.

TABLE 6

Protein Recovery and Coagulation Factors in Plasma Treated with High Intensity Light (Sodium Light (Na) and White Flourescent Light (WL)) (Mean Values; n = 8)

| Joules | PT(sec) | APTT(sec) | TT(sec) | FII(%) | FV(%) | FVII(%) | FX(%) | FVIII(%) | FIX(%) |
|---|---|---|---|---|---|---|---|---|---|
| 0 | 11.6± 02 | 28.6± 0.9 | 13.8± 0.4 | 87.3± 5.1 | 105.3± 11.2 | 90.6± 5.3 | 88.5± 5.2 | 82.4± 11.2 | 89.5± 1.7 |
| 48 WL | 12.6± 0.2 | 37.1± 1.3 | 23.9± 1.5 | 75.4± 3.4 | 82.0± 7.1 | 87.6± 4.4 | 73.6± 2.8 | 55.9± 7.6 | 69.5± 2.6 |
| 60 Na | 12.1± 0.4 | 34.2± 1.3 | 18.2± 2.3 | 80.9± 5.7 | 88.9± 8.8 | 88.3± 5.8 | 79.3± 3.5 | 65.1± 6.3 | 77.6± 4.3 |

| Joules | FXI(%) | FXII(%) | FXIII(%) | VWF(%) | FIB(MG/DL) | TAT(nG/mL) | ATIII(%) | PROTC(%) | PROTS(%) |
|---|---|---|---|---|---|---|---|---|---|
| 0 | 84.6± 3.9 | 89.0± 7.7 | 105.8± 14.8 | 92.4± 16.2 | 272.1± 15.0 | 7.3± 14.1 | 90.4± 10.2 | 93.5± 4.0 | 78.6± 7.6 |
| 48 WL | 52.8± 4.4 | 68.6± 6.2 | 90.4± 6.6 | 94.8± 23.3 | 164.6± 7.3 | 6.5± 12.1 | 79.0± 5.5 | 86.1± 5.3 | 97.5± 9.6 |
| 60 Na | 58.6± 5.5 | 75.3± 7.7 | 91.4± 3.8 | 95.4± 19.4 | 209.3± 22.5 | 6.5± 12.3 | 83.5± 8.1 | 87.5± 4.2 | 96.0± 6.7 |

EXAMPLE 7

Nineteen (19) units of ABO compatible fresh frozen plasma where placed in a 37±2° C. water bath until the plasma had completely thawed. Each unit of plasma was then sequentially sterilely connected to a 3,000 ml Viaflex® container using a Terumo® SCD 312 Sterile Connect Device, and all of the plasma was transferred to the Viaflexs container resulting in Pool A. Additional pools B1 and B2 were prepared in similar fashion.

The Viaflex® container was then sterile connected to eleven 300 ml transfer packs to which approximately 260 ml of plasma was transferred to ten of the packs. The plasma pack was then sterile connected to a disposable tubing set as substantially described in Ser. No. 08/742,572 and the plasma was transferred to a transfer pack containing approximately 97 µg of methylene blue. The remaining transfer pack received 235 ml of plasma. The containers of plasma including methylene blue in a concentration of approximately 1.1 µM were illuminated with sodium light in a light box similar in substantial respects to light box 70 at energy levels of 0, 40, 60, 80 and 100 J/cm$^2$ when measured across the wavelength of 590 to 690 nm. Exposure times were typically between about 200 and 700 seconds. Recovery of Fibrinogen, Factor XI and Factor VIII was measured. The results (mean values) for Fib, F XI and F VIII recovery are set forth in Table 7.

EXAMPLE 8

Figure 17:
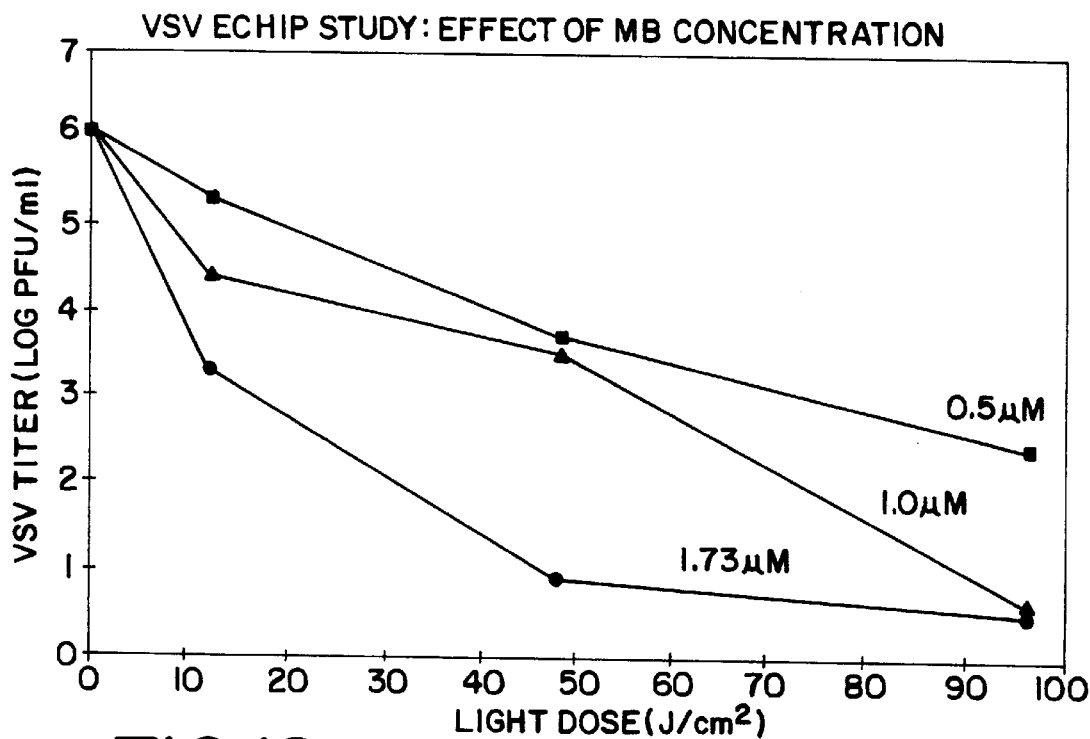
FIG. 17 is a graph showing the effect of photochemical agent concentration on viral inactivation.

Plasma units (approximately 300 ml) spiked with vesicular stomatitis virus (VSV) and including 0.5 µM, 1.0 µM and 1.73 µM concentrations of methylene blue respectively, were treated with sodium light in sodium light box similar in substantial respect to light box 70 described above (using 200W sodium light lamps above and below treatment area 100) described above. The energy dose was measured at various points. After treatment, samples were taken and the samples were titrated by the plaque assay for VSV. The results are reported in FIG. 17. As shown in FIG. 17, increasing the concentration of methylene blue above 1.0 (and to about 1.73) resulted in a significantly improved virucidal effect.

EXAMPLE 9

Figure 18:
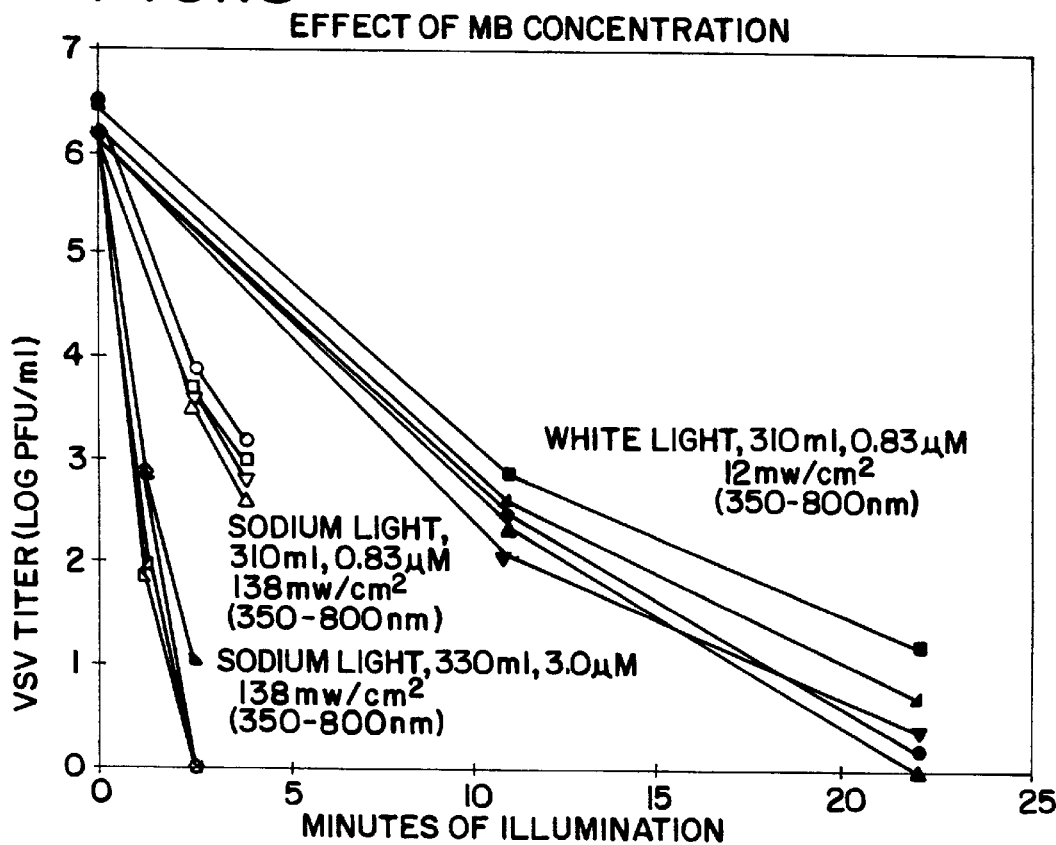
FIG. 18 is another graph showing the effect of photochemical agent concentration on viral inactivation.
Figure 19:
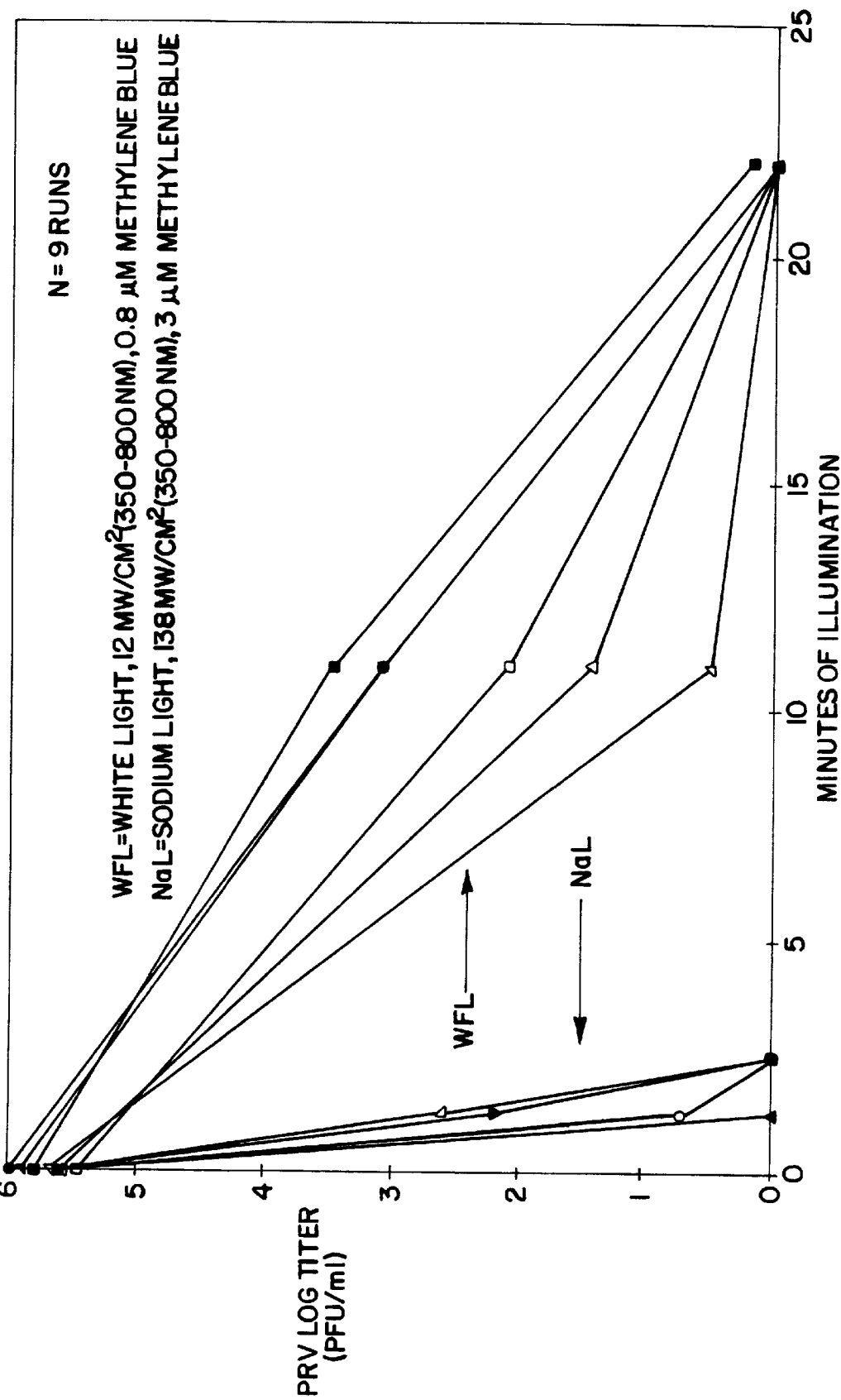
FIG. 19 is another graph also showing the effect of photochemical agent concentration and light intensity on viral inactivation.

Units of plasma spiked with VSV and combined with 3.0 µM or 0.8 µM of methylene blue were treated with sodium light (200W sodium lamps above and below treatment area 100) and/or white flourescent light (white flourescent lamps above and below the treatment area). Specifically, unit 1 included approximately 330 ml of VSV spiked plasma having a 3.0 µM concentration of methylene blue and was treated with sodium light providing an intensity of approximately 138 mw/cm$^2$ (when measured across the range of approximately 350–800 nm), which corresponds to an intensity of approximately 123 mw/cm$^2$ (when measured across the range of approximately 550–700 nm). Unit 2 included approximately 310 ml of VSV spiked plasma having a 0.83 $\mu$M concentration of methylene blue and was also treated with sodium light at the intensities described above. Unit 3 included approximately 310 ml of VSV spiked plasma having a 0.83 $\mu$M concentration of methylene blue and was treated with white flourescent light providing an intensity of approximately 12 mw/cm$^2$ across the range of approximately 350–800 nm which corresponds to 5.2 mw/cm$^2$ across the range of 550–700 nm. Samples were taken and titrated by the plaque assay for VSV. The results set forth in FIG. 18 show a significantly improved virucidal effect after less than 5 minutes in the plasma unit (unit 1) containing a higher concentration (3.0 $\mu$M) of methylene blue and treated with a high intensity light. Additional studies were conducted for plasma spiked with pseudorabies virus (PRV) (a very resistant virus) and the results are shown in FIG. 19. As in Example 8, samples included approximately 3.0 $\mu$M of methylene blue and were treated with high intensity sodium light (approximately 138 mw/cm$^2$ when measured across the range of approximately 350–800 nm, which corresponds to an intensity of approximately 123 mw/cm$^2$ when measured across the range of approximately 550–700 nm). Additional samples including approximately 0.8 $\mu$M of methylene blue were treated with white flourescent light providing an intensity of approximately 12 mw/cm$^2$ across the range of approximately 350–800 nm which corresponds to 5.2 mw/cm$^2$ across the range of 550–700 nm. FIG. 19 shows that a significantly enhanced virucidal effect in less time was achieved when the concentration of methylene blue was increased to approximately 3.0 $\mu$M and a high intensity light was used.

EXAMPLE 10

Figure 20:
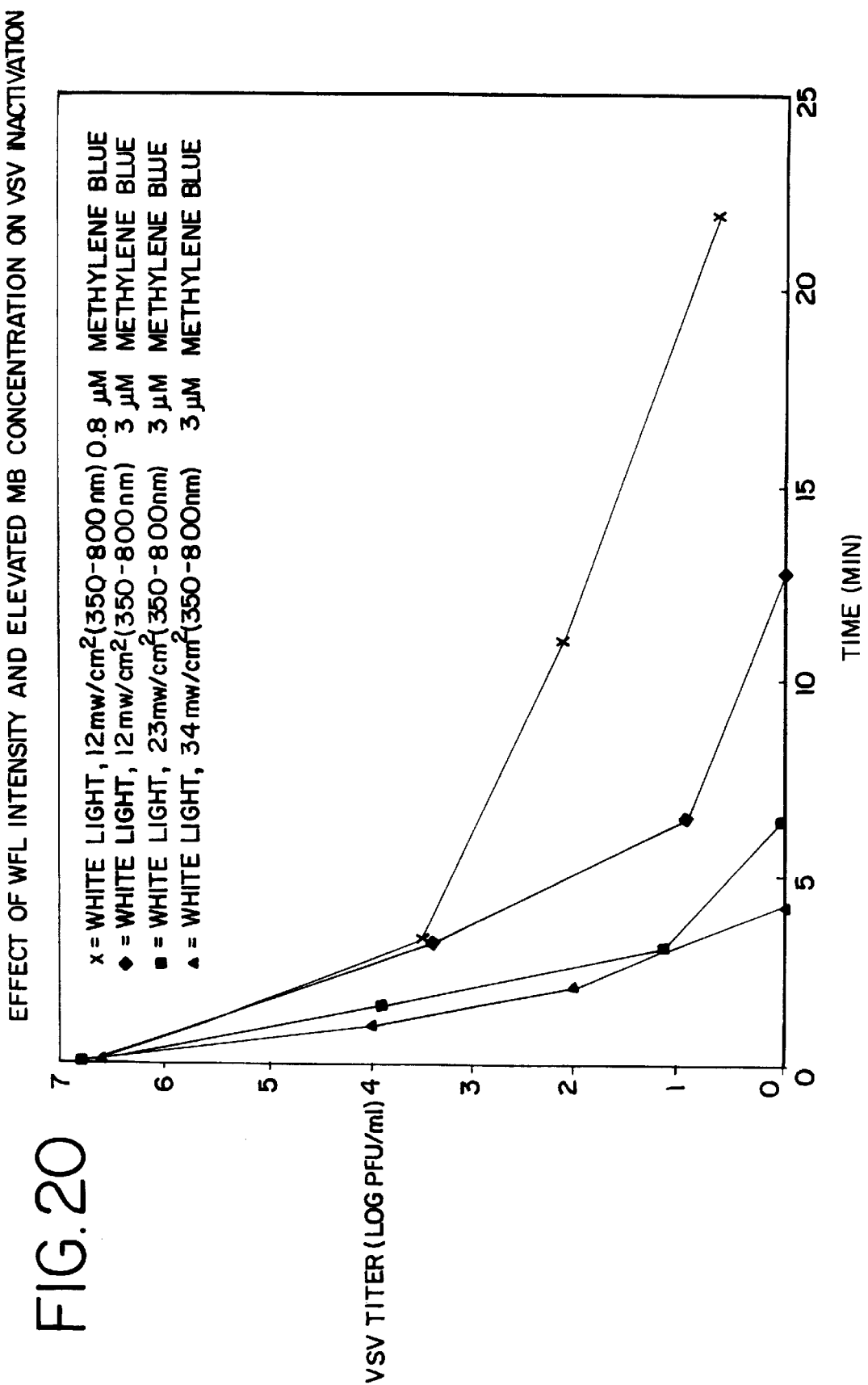
FIG. 20 is another graph showing the effect of photochemical agent concentration and light intensity on viral inactivation.

To further demonstrate the beneficial effect of increasing the methylene blue concentration and light intensity, another experiment was conducted wherein plasma samples (approx. 300 ml) spiked with VSV and having different concentrations (3.0 $\mu$M and 0.8 $\mu$M) of methylene blue were illuminated with white flourescent light at 12, 23 and 34 mw/cm$^2$. Samples were taken and titrated using the plaque assay for VSV. As shown in FIG. 20, the improved virucidal effects (i.e. greater log reduction of virus) was obtained by using a higher concentration of methylene blue. FIG. 20 also shows that using a higher concentration of methylene blue and a higher intensity of light further improves the virucidal effects.

Various modifications of the embodiments and methods described herein are possible in accordance with the scope of the appended claims.

That which is claimed:

1. Apparatus for treating a biological fluid with light comprising:
   a light chamber defined by at least two pair of facing, reflective walls wherein each of said pair of walls substantially defines a compound parabolic curve;
   a high intensity light source disposed within said chamber; and
   a fluid treatment region exterior to said light chamber, said fluid treatment region adapted to hold a quantity of biological fluid.

2. The apparatus of claim 1 wherein said apparatus is adapted to hold at least one flexible container of biological fluid within said fluid treatment region.

3. The apparatus of claim 1 wherein said light source provides a light having an intensity of at least 80 mW/cm$^2$.

4. The apparatus of claim 1 wherein said light source emits at least a portion of its light having wavelengths of between 570 and 690 nm.

5. The apparatus of claim 1 wherein said light source comprises a high pressure sodium light source.

6. The apparatus of claim 1 further comprising a sensor for measuring the amount of light contacting said biological fluid.

7. The apparatus of claim 1 further comprising a control system for ensuring that the amount of light contacting said biological fluid directly from said light source and from said reflective wall surface is at or above a selected minimum.

8. A method for substantially inactivating contaminants in a biological fluid comprising:
   providing a quantity of a biological fluid;
   combining said biological fluid with a selected amount of a phenothiazine dye whereby the concentration of said phenothiazine dye is between approximately 2–4 $\mu$M; and
   contacting said combination of biological fluid and phenothiazine dye with a high intensity light of greater than about 30 mW/cm$^2$.

9. The method of claim 8 wherein said phenothiazine dye comprises methylene blue.

10. The method of claim 8 wherein comprising contacting said combination for a period of time no greater than 5 minutes.

11. The method of claim 8 wherein said light source comprises a high pressure sodium light source.

12. The method of claim 8 further comprising contacting said combination with an amount of light between 35–50 J/cm$^2$.

13. The method of claim 8 wherein said biological fluid comprises blood plasma that is substantially free of red blood cells.

14. The method of claim 13 wherein after contacting, said plasma is substantially free of contaminants and comprises at least 60% of its original fibrinogen, Factor VIII and Factor XI.

15. Apparatus for inactivating contaminants in a biological fluid comprising:
    a first high intensity light source for providing light having an intensity of between approximately 80–150 mW/cm$^2$ in the wavelength range of between approximately 550–700 nm;
    a second high intensity light source for providing light having an intensity of between approximately 80–150 mW/cm$^2$ in the wavelength range of between approximately 550–700 nm; and
    a fluid treatment region located between said first and second light sources, wherein each of said light sources is separated from said fluid treatment region by a window which substantially transmits light in said wavelength range but does not substantially transmit selected unwanted light.

16. Apparatus of claim 15 wherein each of said light sources comprises a high pressure sodium light source.

17. Apparatus of claim 15 further comprising a sensor for monitoring the temperature within said fluid treatment region.

18. Apparatus of claim 15 further comprising a sensor for monitoring the level of useful energy contacting said biological fluid.

19. Apparatus of claim 18 further comprising a control system operably connected to said sensor and to said light sources for ensuring that the level of said useful energy contacting said biological fluid is between about 20 and 50 Joules/cm$^2$.

20. Apparatus of claim 15 further comprising a tray for holding a plastic container of said biological fluid, said tray adapted for movement into and out of said fluid treatment region.

21. Apparatus of claim 15 wherein each of said first and second light sources are housed within a light chamber.

22. Apparatus of claim 21 wherein the interior of said light chamber is comprised of a reflective material.

23. Apparatus of claim 22 wherein the interior of said chamber is defined by at least two pair of facing walls, each of said pair of walls substantially defining a compound parabolic curve.

24. Apparatus of claim 15 wherein said unwanted light comprises light in the infrared light range.

25. Apparatus of claim 24 further comprising a filter for reducing the amount of infrared light contacting said fluid.

26. Apparatus of claim 24 wherein at least a portion of said window is treated with a substance capable of reducing the amount of unwanted light contacting said fluid.

27. Apparatus of claim 24 wherein at least a portion of said window is treated by physical vapor deposition of a material that reduces the amount of unwanted light from contacting said fluid.

28. Apparatus of claim 1 wherein said light source provides light of an intensity between approximately 80–150 mW/cm$^2$.

29. The method of claim 9 wherein the intensity of said light is between approximately 80–150 mW/cm$^2$.

* * * * *